(12) United States Patent
Gulati

(10) Patent No.: US 8,980,874 B2
(45) Date of Patent: Mar. 17, 2015

(54) METHOD AND COMPOSITION FOR TREATING DIABETIC KETOACIDOSIS

(75) Inventor: Anil Gulati, Naperville, IL (US)

(73) Assignee: Midwestern University, Downers Grove, IL (US)

( * ) Notice: Subject to any disclaimer, the term of this patent is extended or adjusted under 35 U.S.C. 154(b) by 645 days.

(21) Appl. No.: 13/266,314

(22) PCT Filed: Apr. 30, 2010

(86) PCT No.: PCT/US2010/033083
§ 371 (c)(1),
(2), (4) Date: Nov. 30, 2011

(87) PCT Pub. No.: WO2010/127197
PCT Pub. Date: Nov. 4, 2010

(65) Prior Publication Data
US 2012/0070513 A1    Mar. 22, 2012

Related U.S. Application Data

(60) Provisional application No. 61/174,283, filed on Apr. 30, 2009.

(51) Int. Cl.
*A61K 31/42* (2006.01)
*A61K 31/4025* (2006.01)
*A61K 31/506* (2006.01)

(52) U.S. Cl.
CPC ............. *A61K 31/4025* (2013.01); *A61K 31/42* (2013.01); *A61K 31/506* (2013.01)
USPC ........................................................ 514/183

(58) Field of Classification Search
None
See application file for complete search history.

(56) References Cited

U.S. PATENT DOCUMENTS 5,922,681 A    7/1999 Doherty et al.

FOREIGN PATENT DOCUMENTS

WO    WO-2008/043102 A2    4/2008

OTHER PUBLICATIONS

Chakrabarti et al (Expert Opin Investig Drugs (Dec. 2000) 9:12, 2873-2888).*
Pannen et al (Hepatology (Mar. 1998) 27:3, 755-764).*
Wikipedia article, "Ketoacidosis" (Sep. 10, 2008) downloaded from https://web.archive.org/web/20080910125816/http://en.wikipedia.org/wiki/Ketoacidosis on Oct. 19, 2014).*
Bonvellet et al (Am J Physiol (1994) 266: H1327-1331).*
Chakrabarti, S. et al., "Therapeutic potential of endothelin receptor antagonists in diabetes," *Expert Opinion on Investigational Drugs*, Dec. 2000, vol. 9, No. 12, pp. 2873-2888.
Pannen, B.H., et al., "Role of endothelins and nitric oxide in hepatic reperfusion injury in the rat," *Hepatology*, Mar. 1998, vol. 27, No. 3, pp. 755-764.
Ruetten, H., et al., "Effects of the endothelin receptor antagonist, SB 209670, on circulatory failure and organ injury in endotoxic shock in the anaesthetized rat," *British Journal of Pharmacology*, May 1996, vol. 118, No. 1, pp. 198-204.
International Search Report in international application No. PCT/US2010/033083, dated Jan. 25, 2011.

* cited by examiner

*Primary Examiner* — Karlheinz R Skowronek
*Assistant Examiner* — Mindy Newman
(74) *Attorney, Agent, or Firm* — Marshall, Gerstein & Borun LLP

(57) ABSTRACT

Methods of treating diabetic ketoacidosis are disclosed. The methods utilize an endothelin antagonist to treat diabetic ketoacidosis in mammals, including humans.

7 Claims, 5 Drawing Sheets

METHOD AND COMPOSITION FOR TREATING DIABETIC KETOACIDOSIS

CROSS-REFERENCE TO RELATED APPLICATIONS

This is the U.S. national phase of International Application No. PCT/US2010/033083, filed Apr. 30, 2010, which claims the benefit of U.S. provisional patent Application No. 61/174,283, filed Apr. 30, 2009, incorporated herein in its entirety by reference.

FIELD OF THE INVENTION

The present invention relates to the treatment of diabetic ketoacidosis using an endothelin receptor antagonist. More particularly, the present invention relates to a method of treating diabetic ketoacidosis by administration of a therapeutically effective amount of an endothelin receptor antagonist to a mammal in need thereof. The composition and method overcome problems and disadvantages associated with present-day treatments for diabetic ketoacidosis.

BACKGROUND OF THE INVENTION

Diabetes affects 23.6 million people per year, with a total estimated cost of $174 billion. Of that cost, 50% is related to in-patient care. Insulin dependent type I diabetes mellitus (TIDM) can be controlled by exogenous insulin. However, poor management of TIDM, failure of the insulin pump to deliver insulin, or prior to a diagnosis of TIDM, glucose levels can rise drastically resulting in a condition called diabetic ketoacidosis (DKA).

DKA accounts for the majority of hospitalizations due to diabetes, especially in children, and accounts for 20% of all deaths related to diabetes (Krane, 1988). DKA is characterized by hyperglycemia (blood glucose levels greater than 250 mg/dL), acidosis (pH less than 7.3), and the presence of ketones in the urine. Patients usually present with dehydration, as seen by hypotension and decreased turgor, extreme thirst due to the high osmolarity of the blood, and in the late stages, vomiting and abdominal pain.

Diagnosing DKA includes assessing the level of consciousness, measuring blood samples for serum or plasma glucose levels, electrolytes, bicarbonate, $pCO_2$, blood urea nitrogen (BUN), creatinine, pH, hemoglobin, and hematocrit (Wolfsdorf et al., 2007). Urinalysis for ketones and an ECG to check for cardiac abnormalities due to altered potassium ion ($K^+$) levels also are monitored (Wolfsdorf et al., 2007). Therapy for DKA includes a correction of dehydration via normal saline (0.9% NaCl) over forty-eight hours, an insulin infusion at 0.1 U/kg/hr, and supportive cardiovascular and respiratory therapy, as needed.

Although these treatments are usually effective, about 0.5-3% of pediatric patients develop cerebral edema (CE), which has a mortality rate of up to 20% (Krane, 1988). For reasons unknown, CE occurs only in pediatric patients. Certain risk factors are associated with the development of CE, including an age of less than five years, severe acidosis as defined by a pH of less than 7.1, low $pCO_2$, and a high BUN (Wolfsdorf et al., 2007). Once identified by the symptoms of headache, bradycardia, changes in neurological status, hypertension, and decreased $O_2$ saturation, the treatment for CE induced by DKA must begin immediately (Vanelli and Chiarelli, 2003; Lam et al., 2005). Treatment includes intravenous mannitol 0.5-1 g/kg over twenty minutes, the reduction of fluid administration by one-third, the administration of a 3% hypertonic saline (5-10 mL/kg over thirty minutes), elevating the head of the bed, and supportive measures to maintain breathing. After the CE has subsided, a head CT scan should be obtained to rule out any neurological sequelae that may result in long term effects such as motor, speech, and learning deficits (Wolfsdorf et al., 2007).

The mechanism for the development of CE is unknown, but several hypotheses have been proposed including an osmotic disequilibrium between the brain and plasma, over-hydration and hyponatremia, intracerebral acidosis induced by alkali therapy (bicarbonate), and alterations in cerebral blood flow (Krane, 1988; Silver et al., 1997; Lam et al., 2005; Wolfsdorf et al., 2007; Yuen et al., 2008). Another possible theory is involvement of rapid insulin and rehydration therapy that leads to the development of CE and its complications, including neurogenic pulmonary edema and detrimental cardiovascular side effects, such as hypertension and increased heart rate (Sherry and Levitsky, 2008).

Endothelin (ET), a twenty-one amino acid vasoconstrictive peptide, elicits a wide range of activities in the body. ET contributes to physiological regulation of the cardiac, pulmonary, renal, and endocrine systems, as well as controlling blood flow to various organs of the body, such as the brain. There are three isoforms of ET: ET-1, ET-2 and ET-3, each of which binds to one of two G-protein coupled receptors, $ET_A$ or $ET_B$ (Yanagisawa et al., 1988a; Yanagisawa et al., 1988b; Gulati et al., 1997b). All isoforms bind with equal affinity to $ET_B$, which is located on endothelial cells. $ET_A$ also binds all ET isoforms; however ET-1 and ET-2 bind equally and preferentially over ET-3. This receptor subtype is located on vascular smooth muscle cells (Said et al., 2005; Sasser et al., 2007).

All three isoforms act on varying physiological systems, and the effects of ET-1 have been studied extensively in diabetic states. Some studies report lower ET-1 levels in children with treated TIDM compared to non-diabetic controls, but other studies show an increase in ET-1 in TIDM patients (Malamitsi-Puchner et al., 1996; Vazquez et al., 1999). There is much conflicting evidence regarding the role of increased or decreased ET-1 and the development of complications associated with TIDM including hypertension, diabetic nephropathy, and stroke. Some studies associate elevated levels of ET-1 with hypertension, reduced renal function, age, and duration of the diabetic state, suggesting that high levels of ET-1 may be implicated in these common complications seen in diabetic patients (Haak et al., 1992). However, other studies show an elevated ET-1 level that does not correlate with hypertension and duration of disease (Takahashi et al., 1990; Schneider et al., 2002). It has been shown that insulin, exogenously or endogenously, increases ET-1 levels (Kirilov et al., 1994; Morise et al., 1995; Ferri et al., 1996). Although ET-1 studies in diabetic states show conflicting evidence regarding whether plasma levels of ET-1 are increased or decreased, it is clear that ET-1 does have an effect on insulin regulation.

In addition to the endocrine system, ET-1 has varying effects on the brain and cerebral vasculature, because increased levels of ET-1 are associated with vasoconstriction in the brain (Zhang et al., 2008). Several studies have shown that cerebral ischemia resulting from an increase in tone of the cerebral vasculature is positively correlated with an increase in ET-1. Increased intracranial pressure (ICP) also is associated with high levels of ET-1, as seen in stroke models of rats. The administration of an $ET_A$ blocking agent decreases ICP, showing a direct correlation with the development of ICP and ET (Lo et al., 2005). Additionally, $ET_A$ receptors have shown to be at increased activity during subarachnoid hemorrhage, which causes an increase in ICP (Lo et al., 2005). Blocking these receptors during increased ICP results in a neuroprotective effect during cerebral ischemia (Zhang et al., 2008). This again supports the observation that ET, specifically, ET-1 and $ET_A$ receptors, are involved in mediating brain blood flow.

Increased ET-1 levels also have been associated with neurogenic pulmonary edema, which can be reversed with BQ123, an $ET_A$ receptor antagonist (Bonvallet et al., 1994). In rats induced with neurogenic pulmonary edema, and the resulting side effects including metabolic acidosis, decreased $pO_2$, increased $pCO_2$, and systemic hypertension, increased levels of ET-1 were observed during a bronchoalveolar lavage. Upon administration of BQ123, the hypoxia and hypercapnea were ameliorated (Herbst et al., 1995). Another study demonstrated that intrathecal (IT) injection of ET-1 into rats resulted in intense pulmonary vasoconstriction, pulmonary edema (PE), and death in some cases. Pre-treatment with BQ123 prevented pulmonary edema and reduced the mortality rate by 50% (Poulat and Couture, 1998). Altered electrical physiological properties in rat myocytes resulting in cardiac arrhythmias have been displayed in rats with T1DM induced by streptozocin (STZ) (Ding et al., 2006). These studies support the theory that increased ET-1 is involved in both CE and PE, and that the administration of an ET antagonist will reduce its resulting side effects of systemic hypertension, hypercapnea, and hypoxia.

ET antagonists are currently being used in research and in clinical application. Many ET antagonists used in the laboratory setting, including BQ-123, BMS-182874, and PD-156707, are $ET_A$ receptor antagonists. BQ-788 and BQ-3020 are selective $ET_B$ antagonists. TAK-044 is a nonselective ET antagonist, blocking the effects of both $ET_A$ and $ET_B$ receptors. Bosentan, a non-selective ET-1 antagonist, blocks the $ET_A$ and $ET_B$ receptors and is currently being used to treat pulmonary hypertension.

SUMMARY OF THE INVENTION

The present invention is directed to a method of treating diabetic ketoacidosis comprising administration of a therapeutically effective amount of an endothelin antagonist to a mammal in need thereof. The present specification shows the involvement of ET-1 in DKA and shows that an ET antagonist can be used in an improved treatment for DKA.

One aspect of the present invention therefore is to provide a method and composition for treating diabetic ketoacidosis, while reducing the occurrence or severity of adverse side effects and complications associated with present day diabetic ketoacidosis treatments. In another embodiment, an endothelin antagonist is administered in conjunction with a second therapy for treating diabetic ketoacidosis or diabetes.

Yet another aspect of the present invention is to provide an article of manufacture for human pharmaceutical use comprising (a) a package insert with instructions for the treatment of diabetic ketoacidosis, (b) a container, and (c) a packaged composition comprising an endothelin antagonist.

These and other aspects of the present invention will become apparent from the following detailed description of the preferred embodiments of the invention.

DETAILED DESCRIPTION OF THE PREFERRED EMBODIMENTS

Figure 1:
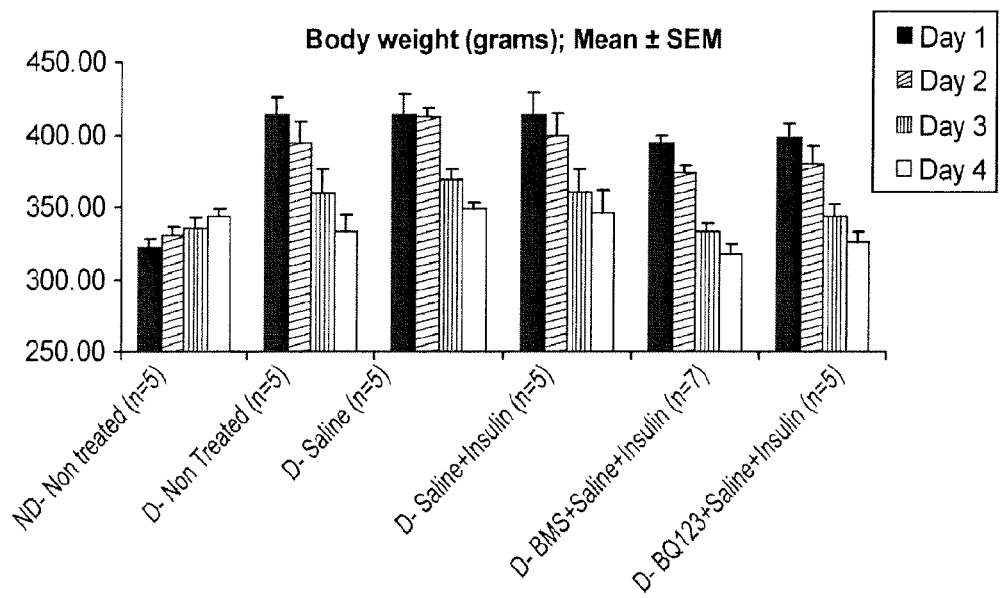
FIG. 1 contains bar graphs showing the body weight (in grams) of treated and untreated rats over a four day treatment period.

The methods described herein benefit from the use of an endothelin antagonist in the treatment of diabetic ketoacidosis. For the purposes of the invention disclosed herein, the term "treatment" includes eliminating, reducing, or ameliorating diabetic ketoacidosis and symptoms associated therewith.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

ET is an extremely potent endothelium derived vasoconstriction factor (Hickey et al., 1985) that was isolated, sequenced, and cloned (Yanagisawa et al., 1988). Endothelins are 21 amino acid, highly potent vasoconstrictive peptides with two disulfide bonds. Endothelins are produced biologically by enzymatically cleaving preproendothelin to proendothelin, then to endothelin by endothelin-converting enzymes. ET exerts biological effects by binding to cell surface receptors, which are 7-transmembrane receptors coupled to G-proteins. There are two distinct types of endothelin receptors: (a) the ET-1 selective $ET_A$ receptors primarily found on vascular smooth muscle and responsible for vasoconstriction, and (b) nonselective $ET_B$ receptors primarily found in vascular endothelium and responsible for vasodilation.

The vasoconstrictive effects of ET-1 are mediated predominantly by G-protein coupled $ET_A$ receptors. ET-1 also is made in high concentrations by prostate, metastatic cancers, and CNS. ET in the CNS is produced by endothelial cells and nonendothelial cells, such as neurons, astrocytes, and glial cells.

The global distribution of ET and its binding sites in the brain suggest that, in addition to being a vasoconstrictor, ET may be acting as an important neuropeptide in the CNS (Gulati et al., 1992). Endothelin (ET) receptor antagonists, in particular selective $ET_A$ or balanced antagonists $ET_A/ET_B$ antagonists, represent a therapeutic area for diseases, such as congestive heart failure (CHF) and pulmonary hypertension. BQ-123 and BMS-182874 are specific antagonists of $ET_A$ receptors (Stein et al., 1994). Endothelin antagonists have profound effects on the pulmonary vasculature and the right heart, whereas ACE inhibitors primarily affect the peripheral vessel and the left heart.

Several studies indicate that the central ET receptors are predominantly of $ET_B$ subtype. Rat cerebral astrocytes have been shown to express mainly $ET_B$ type of receptors and glial cells also were found to intensely express $ET_B$ receptor mRNA. However, the central administration of a highly selective $ET_B$ receptor agonist, IRL-1620, does not produce any effect on the cardiovascular system, and the systemic and regional circulatory effects of centrally administered ET-1 have been shown to be mediated through the $ET_A$ receptors (Gulati et al., 1995; Rebello et al., 1995).

Intracerebroventricular administration of ET-1 produces a transient rise followed by sustained fall in the mean arterial blood pressure (BP). The pressor effect was accompanied by an increase in renal sympathetic nerve activity and plasma levels of catecholamines and arginine-vasopressin.

It also has been shown that the effects of central administration of ET-1 are mediated through activation of the sympathetic nervous system because these effects were attenuated by ganglion blockers. Intracisternal administration of ET-1 elicited a transient increase in BP, renal sympathetic nerve activity, and phrenic nerve activity. A subsequent fall in BP was accompanied by a decrease in renal sympathetic nerve activity and phrenic nerve activity. The observation that central ET-1 induced increase in pressor response was suppressed by pretreatment with phenoxybenzamine (Ouchi et al., 1989), further implicates the active participation of sympathetic nervous system in the initial pressor phase.

An endothelin antagonist utilized in the present invention can be any of the endothelin receptor antagonists known in the art. Endothelin is a potent vasoconstrictor. Endothelin antagonists are used to treat acute heart failure, congestive/chronic heart failure, pulmonary arterial hypertension, pulmonary edema, subarachnoid hemorrhage, chronic obstructive pulmonary disease, myocardial infarction, acute cerebral ischemic, acute coronary syndromes, acute renal failure, post-operative treatment in liver operations, and prostate cancer. No adverse effects are expected when a healthy patient is administered an endothelin antagonist.

In one embodiment, preferred ET antagonists are selective for endothelin A ($ET_A$) receptors or are balanced $ET_A$/endothelin B ($ET_B$) antagonists. Such ET antagonists are set forth in Appendices A and B herein, respectively. However, endothelin B antagonists and miscellaneous endothelin antagonists, as set forth in Appendices C and D herein, respectively, also can be used in a composition or method of the present invention. Additional useful endothelin antagonists can be found in U.S. Patent Application Publication Nos. 2002/0082285 and 2003/0232787, each incorporated herein by reference, and in Wu, *Exp. Opn. Ther. Patents*, 10(11):1653-1668 (2000).

Specific examples of endothelin antagonists useful in the present invention include, but are not limited to, atrasentan, tezosentan, bosentan, sitaxsentan, enrasentan, BMS-207940 (Bristol-Myers Squibb), BMS-193884, BMS-182874, J-104132 (Banyu Pharmaceutical), VML 588/Ro 61-1790 (Vanguard Medica), T-0115 (Tanabe Seiyaku), TAK-044 (Takeda), BQ-788, BQ123, YM-598, LU 135252, PD 145065, A-127722, ABT-627, A-192621, A-182086, TBC3711, BSF208075, S-0139, TBC2576, TBC3214, PD156707, PD180988, ABT-546, ABT-627, Z1611, RPR118031A, SB247083, SB217242, S-Lu302872, TPC10950, SB209670, and mixtures thereof.

BQ123 is a specific endothelin A antagonist, and is the sodium salt of cyclo(-D-Trp-D-Asp-Pro-D-Val-Leu-). BQ-788 is a specific endothelin B antagonist, and is the sodium salt of N-cis-2,6-dimethylpiperidinocarbonyl-L-gamma-methylleucyl-D-1-methoxycarbonyl triptophanyl-DNIe (see *Proc. Natl. Acad. Sci. USA*, 91, pp. 4892-4896 (1994)).

In addition to a conventional endothelin antagonist, a compound that inhibits the formation of endogenous endothelin also can be used as the endothelin antagonist in the present invention. Such compounds are useful because they prevent endothelin formation, and, therefore, decrease the activity of endothelin receptors. One class of such compounds is the endothelin converting enzyme (ECE) inhibitors.

Useful ECE inhibitors include, but are not limited to, CGS34225 (i.e., N-((1-((2(S)-(acetylthio)-1-oxopentyl)-amino)-1-cyclopentyl)-carbonyl-S-4-phenylphenyl-alanine methyl ester) and phosphoramidon (i.e., N-(a-rhamnopyra-nosyloxyhydroxyphosphinyl)-Leu-Trp).

One or more endothelin antagonist can be administered alone to treat diabetic ketoacidosis, or in conjunction with other diabetes and diabetic ketoacidosis therapies, such as insulin, electrolytes, sodium bicarbonate, a diuretic, bumetanide, mannitol, and/or hypertonic saline. The endothelin antagonist also can be administered with fluid therapy for the treatment of diabetic ketoacidosis. The endothelin antagonist can be administered before, after, or simultaneously with insulin, electrolytes, sodium bicarbonate, diuretic, bumetanide, mannitol, and/or hypertonic saline.

The tests and data presented herein show that an endothelin antagonist can be administered to mammals in methods of treating diabetic ketoacidosis. As used herein, the term "endothelin antagonist" means one or more endothelin antagonists, i.e., the present invention encompasses the administration of a single endothelin antagonist or a mixture of endothelin antagonists. The endothelin antagonist can be formulated in suitable excipients for oral administration or for parenteral administration. Such excipients are well known in the art. An endothelin antagonist typically is present in such a composition in an amount of about 0.1% to about 75% by weight.

Pharmaceutical compositions containing the endothelin antagonist are suitable for administration to humans or other mammals. Typically, the pharmaceutical compositions are sterile, and contain no toxic, carcinogenic, or mutagenic compounds that would cause an adverse reaction when administered.

The method of the invention can be accomplished using the endothelin antagonist described above, or as a physiologically acceptable salt or solvate thereof. The endothelin antagonist, salts, or solvates can be administered as the neat compounds, or as a pharmaceutical composition containing either or both entities.

The endothelin antagonist can be administered by any suitable route, for example by oral, buccal, inhalation, sublingual, rectal, vaginal, intracisternal through lumbar puncture, transurethral, nasal, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™. Administration of the endothelin antagonist can be performed before, during, or after the onset of pain.

The pharmaceutical compositions include those wherein the endothelin antagonist is administered in an effective amount to achieve its intended purpose. More specifically, a "therapeutically effective amount" means an amount effective to alleviate or to eliminate diabetic ketoacidosis and symptoms associated therewith. Determination of a therapeutically effective amount is well within the capability of those skilled in the art, especially in light of the detailed disclosure provided herein.

A "therapeutically effective dose" refers to the amount of the endothelin antagonist that results in achieving the desired effect. Toxicity and therapeutic efficacy of the endothelin antagonist can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. A high therapeutic index is preferred. The data obtained can be used in formulating a range of dosage for use in humans. The dosage of the endothelin antagonist preferably lies within a range of circulating concentrations that include the $ED_{50}$ with little or no toxicity. The dosage can vary within this range depending upon the dosage form employed, and the route of administration utilized.

The exact formulation, route of administration, and dosage is determined by an individual physician in view of the patient's condition. Dosage amounts and intervals can be adjusted individually to provide a level of endothelin antagonist that is sufficient to maintain therapeutic or prophylactic effects.

The amount of endothelin antagonist administered is dependent on the subject being treated, on the subject's weight, the severity of the affliction, the manner of administration, and the judgment of the prescribing physician.

Specifically, for administration to a human in the curative treatment of diabetic ketoacidosis, oral dosages of an endothelin antagonist generally is about 10 to about 200 mg daily for an average adult patient (70 kg), typically divided into two to three doses per day. Thus, for a typical adult patient, individual tablets or capsules contain about 0.1 to about 50 mg endothelin antagonist, in a suitable pharmaceutically acceptable vehicle or carrier, for administration in single or multiple doses, once or several times per day. Dosages for intravenous, buccal, or sublingual administration typically are about 0.1 to about 10 mg/kg per single dose as required. In practice, the physician determines the actual dosing regimen that is most suitable for an individual patient, and the dosage varies with the age, weight, and response of the particular patient. The above dosages are exemplary of the average case, but there can be individual instances in which higher or lower dosages are merited, and such are within the scope of this invention.

The endothelin antagonist can be administered alone, or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the endothelin antagonist into preparations that can be used pharmaceutically.

These pharmaceutical compositions can be manufactured in a conventional manner, e.g., by conventional mixing, dissolving, granulating, dragee-making, emulsifying, encapsulating, entrapping, or lyophilizing processes. Proper formulation is dependent upon the route of administration chosen. When a therapeutically effective amount of the endothelin antagonist is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% of an endothelin antagonist of the present invention, and preferably from about 25% to about 90% of an endothelin antagonist of the present invention. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.5% to about 90% by weight of an endothelin antagonist, and preferably about 1% to about 50% of an endothelin antagonist.

When a therapeutically effective amount of the endothelin antagonist is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

An endothelin antagonist can be readily combined with pharmaceutically acceptable carriers well-known in the art. Such carriers enable the endothelin antagonist to be formulated as tablets, pills, dragees, capsules, liquids, gels, syrups, slurries, suspensions and the like, for oral ingestion by a patient to be treated. Pharmaceutical preparations for oral use can be obtained by adding the endothelin antagonist with a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

The endothelin antagonist can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents, such as suspending, stabilizing, and/or dispersing agents.

Pharmaceutical compositions for parenteral administration include aqueous solutions of the endothelin antagonist in water-soluble form. Additionally, suspensions of the endothelin antagonist can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

The endothelin antagonist also can be formulated in rectal compositions, such as suppositories or retention enemas, e.g., containing conventional suppository bases. In addition to the formulations described previously, the endothelin antagonist also can be formulated as a depot preparation. Such long-acting formulations can be administered by implantation (for example, subcutaneously or intramuscularly) or by intramuscular injection. Thus, for example, the endothelin antagonist can be formulated with suitable polymeric or hydrophobic materials (for example, as an emulsion in an acceptable oil) or ion exchange resins, or as sparingly soluble derivatives, for example, as a sparingly soluble salt.

In particular, the endothelin antagonist can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. An endothelin antagonist also can be injected parenterally, for example, intravenously, intramuscularly, subcutaneously, intrathecally, intracisternally, or intracoronarily. For parenteral administration, the endothelin antagonist is best used in the form of a sterile aqueous solution which can contain other substances, for example, salts or monosaccharides, such as mannitol or glucose, to make the solution isotonic with blood.

For veterinary use, the endothelin antagonist is administered as a suitably acceptable formulation in accordance with normal veterinary practice. The veterinarian can readily determine the dosing regimen and route of administration that is most appropriate for a particular animal.

It has been discovered that using an endothelin antagonist used in combination with insulin provides an effective treatment for diabetic ketoacidosis which avoids the adverse effects and complications associated with present day treatments for diabetic ketoacidosis.

The involvement of endothelin (ET) in a rat model of DKA was studied. DKA was produced by intraperitoneal injection of streptozotocin (150 mg/kg). Blood glucose and ketones were significantly increased and pH was decreased on day 4 indicating development of diabetic ketoacidosis. All experiments were conducted on day 4. Body weight, blood glucose, urinary ketone, blood ketone, arterial blood gases, blood electrolytes, mean arterial pressure, pulse pressure, heart rate, brain blood perfusion, brain and lung water content were determined before and after following treatments: non-diabetic untreated (control); diabetic untreated (positive control); diabetic saline treated; diabetic saline+insulin treated; and diabetic BMS-182874 ($ET_A$ receptor antagonist)+saline+insulin treated. An $ET_A$ receptor antagonist, BMS-182874, produced an improvement in arterial blood pH (from 6.82±0.02 to 6.91±0.02), blood $K^+$ levels (from 4.21±0.33 to 2.75±0.27 mmol/dL), and blood lactate levels (from 2.74±0.64 to 1.57±0.20 mg/dL). BMS-182874 also prevented development of insulin induced hypertension and increase in cerebral blood perfusion. Results show that endothelin antagonists, like $ET_A$ receptor antagonists, are of therapeutic use in the management of diabetic ketoacidosis.

Materials and Methods
Animals

Male Sprague-Dawley rats weighing 300 to 350 g (Harlan, Indianapolis, Ind.) were housed for at least 4 days before being used in a room with controlled temperature (23±1° C.), humidity (50±10%), and light (6:00 A.M. to 6:00 P.M.). Food and water were made available continuously. Animal care and use for experimental procedures were approved by the Institutional Animal Care and Use Committee (IACUC). All anesthetic and surgical procedures were in compliance with the guidelines established by the Animal Care Committee.

Drugs and Chemicals

Streptozotocin, urethane (Sigma-Aldrich St Louis, Mo., USA); BMS-182874 hydrochloride (5-Dimethylamino)-N-(3,4-dimethyl-5-isoxazolyl)-1-naphthalene sulfonamide hydrochloride) and BQ123 Cyclo(D-Trp-D-Asp-Pro-D-Val-Leu) an $ET_A$-specific antagonists (Tocris Bioscience, Ellisville, Mo., USA); Endothelin-1 (Research Biochemicals International, Natick, Mass., USA); and Endothelin-1 Enzyme Immunometric Assay (EIA) Kit (Catalog No. 900-020A, Assay Designs, Inc., Ann Arbor, Mich., USA). Other reagents used were of the highest grade commercially available.

Induction of Diabetic Ketoacidosis (DKA)

Normotensive Sprague Dawley rats were kept on fasting for 2 hours with unlimited access to water. After 2 hours of fasting, rats were injected intraperitoneally with 150 mg/kg of streptozotocin in 0.05 mol/L citric acid, pH 4.3 to induced diabetes (Lam et al., 2005; Yuen et al., 2008), while non-diabetic control rats received an intraperitoneal injection of 0.05 mol/L citrate buffer (Lam et al., 2005; Yuen et al., 2008). Rats were allowed unlimited access to tap water and food. Each day rats were weighed and urine ketone levels were estimated by Urine Reagent Strips, 1K Parameter. Prior to streptozotocin or citrate buffer injection, baseline blood glucose levels were assessed by One Touch Ultra blood glucose strips from Lifescan, Milpitas, Calif., and baseline blood ketone levels were estimated using Cardiochek blood ketone analyzer. Blood glucose and ketone were measured again on day three and four to ensure the onset of hyperglycemia and ketoacidosis. Significantly elevated (1) urine ketone levels (>160 mg/dL), (2) ketone levels in blood (>20 mg/dL), and (3) blood glucose levels (>400 mg/dL) developed on day four after streptozotocin injection indicating the development diabetic ketoacidosis (DKA) in rats. Blood samples were withdrawn from the femoral vein for baseline reading prior to start of treatment, after the first hour of treatment, and then at the end of the treatment (fifth hour of experiment).

Determination of Blood Gases

Arterial blood pH, $pO_2$, $pCO_2$, $Na^+$, $K^+$, lactate, and hematocrit were monitored prior to, at one hour, and at the end of treatment. Blood samples were drawn from the arterial cannula using blood gas sampling syringes (Innovative Medical Technologies, Inc. Leawood, Kans.) and analyzed using a GEM Premier 3000 unit (Instrument Laboratory, Lexington, Mass.). Blood samples were withdrawn from the femoral artery for baseline reading prior to start of treatment, after the first hour of treatment, and then at the end of the treatment (fifth hour of experiment).

Determination of Brain Blood Perfusion

A burr hole was drilled into the rat skull approximately 2 millimeters (mm) to the left of midline, being careful not to disturb the brain tissue itself. Cerebrovascular perfusion was measured via a fiber optic probe (PF407) applied to the surface of the rat brain. The probe was connected to a Periflux PF2b 4000 Laser Doppler Flowmetry unit (Perimed, Stockholm, Sweden). The perfusion was determined by measuring the passage of red blood cells through the capillaries.

Determination of Cardiovascular Parameters

Rats were anaesthetized with urethane (1.5 g/kg ip.) and prepared for the determination of hemodynamic parameters (Gulati et al., 1997a; Gulati et al., 1997b). The anesthetized rats were shaved and immobilized to prepare for cannulation. A 2-3 centimeter (cm) incision was made above the femoral vein and artery and the vessels were dissected and cleaned. The left femoral vein was cannulated (PE-50 tubing, Clay Adams, Parsipanny, N.J.) and secured for drug administration. An ultra-miniature pressure transducer SPR-320 (2F Polyurethane), with a single pressure sensor side mounted at the tip (Millar Instruments, Houston, Tex.) was inserted in the left femoral artery to acquire the hemodynamic signals. Pressure transducer was connected to bridge amplifier (ML221 Bridge Amp; AD Instruments, Mountain View, Calif., USA) with Viking connector (AEC-10C) and the signals were continuously acquired at a sampling rate of 1000 $S^{-1}$ using Millar PowerLab 16/30 data acquisition system (AD Instruments, Mountain View, Calif., USA). Mean arterial pressure (MAP), heart rate (HR), and pulse pressure (PP) were determined and analyzed with LabChart-5.00 software program (Millar Instruments). After the experiment was completed, the animals were euthanized with a high dose of urethane (3 gm/kg).

Determination of Brain and Lung Water Content

Water content in the lung and brain was determined to assess brain and pulmonary edema. Assessment of brain and lung water content was carried out as follows. At the end of treatment the animal was sacrificed and trachea was immediately tied, then the lungs were dissected out. The skull was opened and brain dissected out. Brain and lungs were rinsed with saline, and weighed (wet weight). The brain and lungs were kept for drying in an oven at a temperature of 60° C. for 72 hours, then weighed again (dry weight). The percent water content was calculated using the formula: [(wet weight−dry weight)/wet weight×100].

Determination of ET-1 Level in Plasma

In order to analyze the change in plasma ET-1 level during the treatment, blood samples were withdrawn through right femoral artery of the rats before and at the end of experiment and were collected into chilled EDTA tubes (1 mg/mL blood) containing aprotinin (500 KIU/mL of blood). The blood samples were centrifuged at 1,600×g for 15 minutes at 0° C. and plasma separated was stored at −70° C. until analyzed. ET-1 level was estimated using Assay's Design's Endothelin-1 Enzyme Immunometric Assay Kit (Nowicki et al., 2005; Brondani et al., 2007). Briefly, plasma samples and standards were added to wells coated with a monoclonal antibody specific for ET-1. The plate then was washed after 24 hours of incubation, leaving only bound ET-1 on the plate. A solution of horseradish peroxidase (HRP) labeled monoclonal antibody to ET-1 then was added, which binds to the ET-1 captured on the plate. The plate was incubated for 30 min, then washed to remove excess HRP labeled antibody. A solution of 3,3',5,5'-tetramethylbenzidine (TMB) substrate was added, which generates a blue color when catalyzed by the HRP. Hydrochloric acid (1N) was added to stop the substrate reaction, and the resulting yellow color was read at 450 nm using DTX 800 Multimode detector. The data was analyzed with Multimode Detection Software (Beckman Coulter, Inc., Fullerton, Calif.). The measured optical density is directly proportional to the concentration of ET-1 in either standards/plasma. Blood samples from all the groups were collected before the start and at end of the treatment.

Study Design

The animals were allowed to stabilize for at least 20 minutes following surgical procedures. Body weight, blood glucose, urinary ketone, blood ketone, arterial blood gases, blood electrolytes, mean arterial pressure, pulse pressure, heart rate, brain blood perfusion, brain and lung water content were determined in the following groups Group 1: Non-diabetic untreated (Non-D-Untreated): Rats were injected with citrate buffer (1 ml/kg ip) on day one and studies were performed on day four.

Group 2: Diabetic untreated (D-Untreated): Rats were injected with streptozotocin in citrate buffer (150 mg/kg ip) to induce diabetes and ketoacidosis. Rats were given no treatment.

Group 3: Diabetic saline treated (D-Saline treated): Rats were injected with streptozotocin in citrate buffer (150 mg/kg ip) to induce diabetes and ketoacidosis. Rats were treated with saline. Saline was infused using an infusion pump (Harvard Apparatus Infusion/Withdrawal Pump, Millis, Mass.) via cannulated femoral vein with saline (0.9% NaCl; Hospira, Incorporated, Lake Forest, Ill.) at 80 mL/kg/hr for one hour. During the next two through four hours, rats were administered saline at 40 mL/kg/hr (Yuen et al., 2008).

Group 4: Diabetic saline/insulin treated (D-Saline+insulin treated): Rats were injected with streptozotocin in citrate buffer (150 mg/kg ip) to induce diabetes and ketoacidosis. On day three, rats were treated with 1.5 U/kg regular insulin (Humulin® R (Regular human insulin, rDNA origin). On day four, saline and insulin treatment was carried out. Rats were infused via cannulated femoral vein saline, 0.9% NaCl at 80 mL/kg/hr and 1.5 U/kg/hr regular insulin for one hour. During the next two through four hours, rats were infused with saline, 0.9% NaCl at 40 mL/kg/hr and 1.5 U/kg/hr regular insulin (Yuen et al., 2008).

Group 5: Diabetic BMS-182874/saline/insulin treated (D-BMS+Saline+insulin treated): Rats were injected with streptozotocin in citrate buffer (150 mg/kg ip) to induce diabetes and ketoacidosis. On day three, rats were treated with 1.5 U/kg regular insulin. On day four, rats were administered a bolus dose of selective $ET_A$ receptor antagonist, BMS-182874 (9 mg/kg), then saline and insulin treatment was carried out. Rats were infused via cannulated femoral vein saline, 0.9% NaCl at 80 mL/kg/hr and 1.5 U/kg/hr regular insulin for one hour. During the next two through four hours rats were infused with saline, 0.9% NaCl at 40 mL/kg/hr and 1.5 U/kg/hr regular insulin.

Group 6: Diabetic BQ123/saline/insulin treated (D-BQ+saline+insulin treated): Same as above for Group 5, except BQ123 (1 mg/kg body weight) is used as a substitute for BMS-182874 (9 mg/kg).

Data are presented as mean±SEM. The significance of differences was estimated by one-way analysis of variance (intra group comparison with respect to base line data) and two-way analysis of variance (inter group comparison with respect to corresponding time points from each groups) followed by application of the Dunnett's Multiple Comparisons and Bonferroni test respectively. A P value of less than 0.05 was considered to be significant. The statistical analysis was processed with GraphPad Prism software Version 5.00.

Results

Table 1 shows the effect of induction of diabetic ketoacidosis and treatment on blood glucose (mg/dL) levels in various groups of rats. *P<0.05 compared to day 1 and #P<0.05 compared to day 4 pretreatment. The results show that induction of diabetic ketoacidosis by streptozotocin increased blood glucose levels, and that treatment with insulin produced a significant decrease in blood glucose. It also was found that surgical procedures significantly increased blood glucose levels. Treatment with BMS-182874 or BQ123 did not significantly affect blood glucose.

| Study groups | Day 1 | Day 3 | Day 4 (pre-tx) | Day 4 (1 hour of tx) | Day 4 (end of tx) |
|---|---|---|---|---|---|
| ND-Not treated (N = 4) | 86 ± 2 | 94 ± 1 | 97 ± 3 | 258 ± 66 | 223 ± 51 |
| D-Non treated (N = 5) | 94 ± 3 | 404 ± 8* | 525 ± 20 | 523 ± 25* | 521 ± 20* |
| D-Saline (N = 5) | 85 ± 3 | 369 ± 10* | 480 ± 27 | 383 ± 23* | 344 ± 21* |
| D-Saline + Insulin (N = 5) | 92 ± 6 | 428 ± 10* | 530 ± 20 | 444 ± 26* | 200 ± 20*# |
| D-BMS + Saline + Insulin (N = 7) | 87 ± 3 | 429 ± 12* | 522 ± 18* | 446 ± 36* | 263 ± 32*# |
| D-BQ123 + Saline + Insulin (N = 5) | 94 ± 5 | 434 ± 19* | 484 ± 17* | 462 ± 55* | 312 ± 55*# |

Table 2 shows the effect of induction of diabetic ketoacidosis and treatment on blood ketone levels (mg/dL) levels in various groups of rats. *P<0.05 compared to day 1 and #P<0.05 compared to day 4 pretreatment. The results show that induction of diabetic ketoacidosis by streptozotocin increased blood ketone levels, and that insulin treatment with and without BMS-182874/BQ123 produced a significant decrease in blood ketones. Treatment with BMS-182874 did not significantly affect blood ketones. Treatment with BQ123 significantly decrease the blood ketones. Please see FIG. 2.

| Study groups | Day 1 | Day (pre tx) | Day 4 (end of tx) |
|---|---|---|---|
| ND-Not treated (N = 8) | 3.16 ± 0.25 | 3.47 ± 0.34 | 4.43 ± 0.49 |
| D-Non treated (N = 5) | 2.86 ± 0.16 | 37.28 ± 1.39* | 33.62 ± 2.66* |
| D-Saline (N = 5) | 2.76 ± 0.30 | 41.64 ± 2.27* | 32.04 ± 4.16* |
| D-Saline + Insulin (N = 4) | 2.65 ± 0.27 | 31.925 ± 5.28* | 12.8 ± 4.04*# |
| D-BMS + Saline + Insulin (N = 7) | 2.85 ± 0.19 | 31.01 ± 2.29* | 14.65 ± 2.70*# |
| D-BQ123 + Saline + Insulin (N = 4) | 2.9 ± 0.25 | 28.22 ± 3.14* | 5.2 ± 0.36*# |

Table 3 shows the effect of induction of diabetic ketoacidosis and treatment on urine ketone levels (mg/dL) levels in various groups of rats. *P<0.05 compared to day 1. The results show that induction of diabetic ketoacidosis by streptozotocin increased urine ketone levels. Because urine ketones were determined before the start of any treatment, the effect of treatment is not observed in this study.

| Study groups | Day 1 | Day 3 | Day 4 (pre tx) |
|---|---|---|---|
| ND-Not treated (N = 8) | 3.125 ± 0.91 | 3.75 ± 0.81 | 4.37 ± 0.62 |
| D-Non treated (N = 5) | 2.00 ± 1.22 | 160 ± 0* | 160 ± 0* |
| D-Saline (N = 5) | 3.00 ± 1.22 | 160 ± 0* | 160 ± 0* |
| D-Saline + Insulin (N = 4) | 6.00 ± 0.00 | 104 ± 19.64* | 160 ± 0* |
| D-BMS + Saline + Insulin (N = 7) | 6.42 ± 1.12 | 125.71 ± 16.13* | 160 ± 0* |
| D-BQ123 + Saline + Insulin (N = 5) | 3.00 ± 1.03 | 80 ± 0* | 160 ± 0* |

Table 4 shows the effect of induction of diabetic ketoacidosis and treatment on plasma ET-1 (pg/mL) levels in various groups of rats. *P<0.05 compared to pretreatment and #P<0.05 compared to Non-D-untreated group. It can be concluded that (1) induction of diabetic ketoacidosis and (2) insulin treatment increased the plasma levels of ET-1. It also was found that surgical procedures significantly increased plasma ET-1 levels. Treatment with BMS-182874 or BQ123 did not significantly affect plasma ET-1 level.

| Study Groups | Day 4 (pre tx) | Day 4 (end of tx) |
|---|---|---|
| Non-D-Untreated | 6.79 ± 1.77 | 14.94 ± 2.22* |
| D-Untreated | 9.15 ± 1.03# | 17.82 ± 2.02* |
| D-Saline treated | 8.34 ± 0.65 | 11.86 ± 1.04* |
| D-Saline/Insulin treated | 11.76 ± 1.94# | 22.17 ± 2.67*# |
| D-BMS/Saline/Insulin-Treated | 11.93 ± 2.01# | 20.40 ± 3.23*# |
| D-BQ123/Saline/Insulin-Treated | 15.78 ± 4.11# | 26.53 ± 5.52*# |

Table 5 shows the effect of induction of diabetic ketoacidosis and treatment on arterial blood pH in various groups of rats. *P<0.05 compared to non-diabetic untreated rats and #P<0.05 compared to diabetic-saline+insulin treated rats. The results show that induction of diabetic ketoacidosis by streptozotocin decreased pH indicating development of severe acidosis. Saline or saline+insulin treatment did not produce any significant improvement in acidosis. However, treatment with BQ123 or BMS-182874+saline+insulin produced a significant improvement in arterial blood pH. Results indicate that an $ET_A$ receptor antagonist, e.g., BMS-182874 or BQ123, can be used to improve acidosis during treatment of diabetic ketoacidosis. The instrument could not record pH readings below 6.80.

| Study groups | Day 4 (pre-tx) | Day 4 (1 hour of tx) | Day 4 (end of tx) |
|---|---|---|---|
| Non-D-Untreated (N = 7) | 7.31 ± 0.02 | 7.26 ± 0.02 | 7.17 ± 0.04 |
| D-Untreated (N = 5) | 6.80 ± 0.00* | 6.80 ± 0.00* | 6.80 ± 0.00* |
| D-Saline treated (N = 5) | 6.85 ± 0.02* | 6.84 ± 0.02* | 6.84 ± 0.02* |
| D-Saline-Insulin treated (N = 5) | 6.81 ± 0.01* | 6.80 ± 0.01* | 6.81 ± 0.04* |
| D-BMS-Saline-Insulin (N = 7) | 6.82 ± 0.02* | 6.81 ± 0.01* | 6.91 ± 0.02*# |
| D-BQ123-Saline-Insulin (N = 5) | 6.82 ± 0.02* | 6.81 ± 0.01* | 6.91 ± 0.01*# |

Table 6 shows the effect of induction of diabetic ketoacidosis and treatment on arterial blood $pCO_2$ (mmHg) in various groups of rats. *P<0.05 compared to non-diabetic untreated rats. The results show that induction of diabetic ketoacidosis by streptozotocin decreased arterial blood $pCO_2$. There is no change in arterial blood $pCO_2$ during various treatments.

| Study groups | Day 4 (pre-tx) | Day 4 (1 hour of tx) | Day 4 (end of tx) |
|---|---|---|---|
| Non-D-Untreated (N = 7) | 43.66 ± 5.68 | 45.85 ± 2.35 | 61.28 ± 3.78 |
| D-Untreated (N = 5) | 24.80 ± 1.77* | 20.80 ± 3.16* | 19.80 ± 1.83* |
| D-Saline treated (N = 5) | 22.00 ± 3.44* | 24.60 ± 3.51* | 21.80 ± 2.31* |
| D-Saline-Insulin treated (N = 5) | 30.40 ± 2.46* | 29.00 ± 2.30* | 27.60 ± 2.21* |
| D-BMS-Saline-Insulin (N = 7) | 28.71 ± 2.08* | 30.57 ± 1.94* | 30.57 ± 2.23* |
| D-BQ123-Saline-Insulin (N = 5) | 25.00 ± 3.7* | 23.6 ± 2.17* | 23.2 ± 1.95* |

Table 7 shows the effect of induction of diabetic ketoacidosis and treatment on arterial blood $pO_2$ (mmHg) in various groups of rats. *P<0.05 compared to non-diabetic untreated rats. The results show that induction of diabetic ketoacidosis by streptozotocin increased arterial blood $pO_2$. There is no change in arterial blood $pO_2$ during various treatments.

| Study groups | Day 4 (pre-tx) | Day 4 (1 hour of tx) | Day 4 (end of tx) |
|---|---|---|---|
| Non-D-Untreated (N = 7) | 107.66 ± 5.67 | 108.00 ± 7.25 | 101.00 ± 9.62 |
| D-Untreated (N = 5) | 161.20 ± 7.47* | 173.60 ± 12.64* | 145.60 ± 9.79* |
| D-Saline treated (N = 5) | 148.20 ± 4.40* | 150.80 ± 8.45* | 154.40 ± 5.83* |
| D-Saline-Insulin treated (N = 5) | 145.00 ± 10.84* | 160.20 ± 11.36* | 155.60 ± 11.43* |
| D-BMS-Saline-Insulin (N = 7) | 156.71 ± 7.11* | 135.57 ± 6.37* | 143.85 ± 6.59* |
| D-BQ123-Saline-Insulin (N = 5) | 130.2 ± 14.04* | 128.4 ± 11.006* | 141.2 ± 4.6* |

Table 8 shows the effect of induction of diabetic ketoacidosis and treatment on blood $Na^+$ (mmol/L) level in various groups of rats. The results show that induction of diabetic ketoacidosis by streptozotocin did not produce any change in blood sodium ion ($Na^+$) levels. There is no change in blood $Na^+$ levels during various treatments.

| Study groups | Day 4 (pre-tx) | Day 4 (1 hour of tx) | Day 4 (end of tx) |
|---|---|---|---|
| Non-D-Untreated (N = 7) | 142.50 ± 2.02 | 141.57 ± 1.39 | 137.85 ± 1.65 |
| D-Untreated (N = 5) | 133.80 ± 1.80 | 138.60 ± 1.97 | 131.40 ± 4.12 |
| D-Saline treated (N = 5) | 138.80 ± 2.66 | 141.40 ± 2.50 | 144.60 ± 1.91 |
| D-Saline-Insulin treated (N = 5) | 135.00 ± 2.17 | 141.60 ± 1.21 | 148.60 ± 0.51 |
| D-BMS-Saline-Insulin (N = 7) | 135.71 ± 2.06 | 143.42 ± 1.84 | 146.14 ± 1.14 |
| D-BQ123-Saline-Insulin (N = 5) | 140.00 ± 2.87 | 147 ± 1.3 | 150.04 ± 2.43 |

Table 9 shows the effect of induction of diabetic ketoacidosis and treatment on blood $K^+$ (mmol/L) level in various groups of rats. *$P<0.05$ compared to non-diabetic untreated rats and #$P<0.05$ compared to diabetic untreated rats. The results show that induction of diabetic ketoacidosis by streptozotocin produces an increase in blood $K^+$ (potassium ion) levels. Treatment with saline+insulin or BMS-182874+saline+insulin or BQ123-Saline-Insulin significantly reduced the change in blood $K^+$ levels induced by diabetic ketoacidosis. Hyperkalemia is commonly found in cases of DKA (Fulop, 1979), which causes $K^+$ to redistribute from intracellular to extracellular fluid, and can lead to U-waves and flattened T-waves on the EKG (Malone and Brodsky, 1980). When insulin is infused hypokalemia can result which produces a profound risk of arrhythmias. BMS-182874 and BQ123 have been found to produce hemodynamic stability, and can be used to prevent adverse cardiovascular events.

| Study groups | Day 4 (pre-tx) | Day 4 (1 hour tx) | Day 4 (end of tx) |
|---|---|---|---|
| Non-D-Untreated (N = 7) | 3.28 ± 0.17 | 3.64 ± 0.26 | 4.5 ± 0.21 |
| D-Untreated (N = 5) | 5.12 ± 0.23* | 6.08 ± 0.88* | 6.96 ± 0.77* |
| D-Saline treated (N = 5) | 5.02 ± 0.83* | 5.04 ± 0.80* | 5.74 ± 0.74* |
| D-Saline-Insulin treated (N = 5) | 3.82 ± 0.29 | 2.92 ± 0.16# | 2.48 ± 0.24# |
| D-BMS-Saline-Insulin (N = 7) | 4.21 ± 0.33 | 2.62 ± 0.29# | 2.75 ± 0.27# |
| D-BQ123-Saline-Insulin (N = 5) | 3.4 ± 0.45 | 2.04 ± 0.29# | 2.38 ± 0.34# |

Table 10 shows the effect of induction of diabetic ketoacidosis and treatment on blood lactate (mg/dL) level in various groups of rats. *$P<0.05$ compared to non-diabetic untreated rats and #$P<0.05$ compared to diabetic untreated rats. The results show that induction of diabetic ketoacidosis by streptozotocin produces an increase in blood lactate levels. Treatment with saline, saline+insulin, or BMS-182874+saline+insulin, or BQ123+saline+insulin significantly reduced the change in blood lactate levels induced by diabetic ketoacidosis.

| Study groups | Day 4 (pre-tx) | Day 4 (1 hour of tx) | Day 4 (end of tx) |
|---|---|---|---|
| Non-D-Untreated (N = 7) | 2.11 ± 0.35 | 1.84 ± 0.20 | 1.88 ± 0.37 |
| D-Untreated (N = 5) | 1.66 ± 0.23 | 2.30 ± 0.41* | 3.78 ± 0.37* |
| D-Saline treated (N = 5) | 1.88 ± 0.28 | 1.56 ± 0.29 | 1.26 ± 0.40# |
| D-Saline-Insulin treated (N = 5) | 2.50 ± 0.47 | 1.54 ± 0.47 | 1.00 ± 0.20# |
| D-BMS-Saline-Insulin (N = 7) | 2.74 ± 0.64 | 1.21 ± 0.13# | 1.57 ± 0.20# |
| D-BQ123-Saline-Insulin (N = 5) | 2.7 ± 0.92 | 1.48 ± 0.45# | 1.8 ± 0.3# |

Table 11 shows the effect of induction of diabetic ketoacidosis and treatment on blood hematocrit (Hct; %) in various groups of rats. #$P<0.05$ compared to diabetic untreated rats. The results show that induction of diabetic ketoacidosis by streptozotocin produces no change in hematocrit. Treatment with saline+insulin or BMS+saline+insulin or BQ123+saline+insulin significantly reduced the hematocrit.

| Study groups | Day 4 (pre-tx) | Day 4 (1 hour of tx) | Day 4 (end of tx) |
|---|---|---|---|
| Non-D-Untreated (N = 7) | 40.66 ± 4.07 | 39.71 ± 2.08 | 43.14 ± 2.46 |
| D-Untreated (N = 5) | 51.80 ± 1.65 | 47.00 ± 1.58 | 46.40 ± 0.92 |
| D-Saline treated (N = 5) | 46.40 ± 1.33 | 41.20 ± 3.23 | 39.80 ± 1.11 |
| D-Saline-Insulin treated (N = 5) | 49.80 ± 2.27 | 38.80 ± 1.80 | 30.20 ± 3.12# |
| D-BMS-Saline-Insulin (N = 7) | 45.71 ± 1.48 | 33.28 ± 1.52# | 29.28 ± 2.22# |
| D-BQ123-Saline-Insulin (N = 5) | 42.6 ± 4.81 | 31.4 ± 2.97# | 31.8 ± 2.21# |

FIG. 1 shows the effect of induction of diabetic ketoacidosis and treatment on body weight (grams) in various groups of rats. The results show that, over 4 day period, body weight increased in control rats without diabetic ketoacidosis. Induction of diabetic ketoacidosis by streptozotocin produced a similar decrease in body weight over 4 day period in all the treatment groups.

Figure 2:
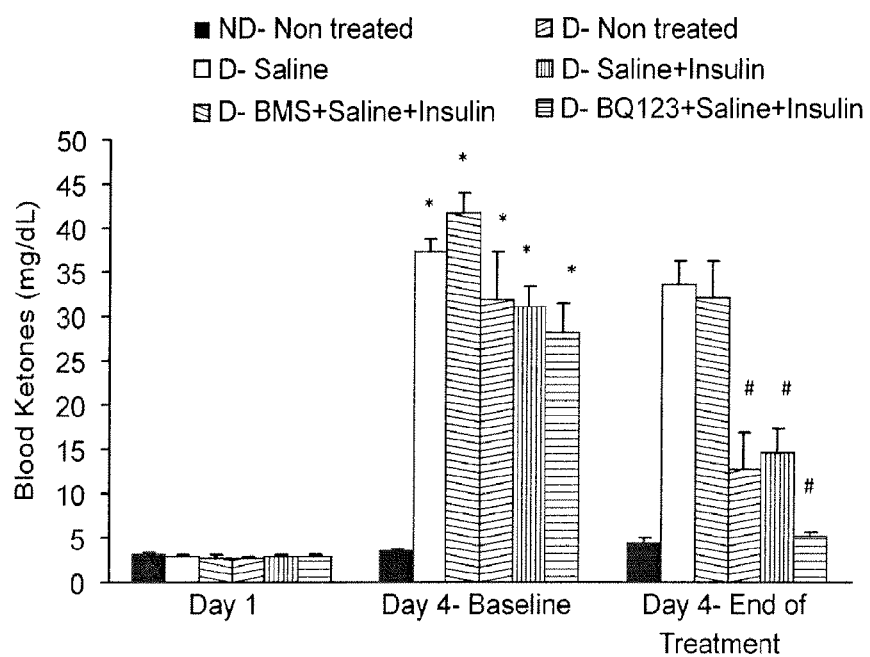
FIG. 2 contains bar graphs showing the blood ketone content (in mg/dL) of treated and untreated rats over a four day treatment period.

FIG. 2 shows the effect of induction of diabetic ketoacidosis and treatment on blood ketone levels (mg/dL) levels in various groups of rats. The results show that induction of diabetic ketoacidosis by streptozotocin increased blood ketone levels. Saline+insulin treatment, as well as BQ123 or BMS+saline+insulin treatment, produced a significant decrease in blood ketones. BQ123+saline+insulin treatment provided a particularly marked decrease in blood ketones of DKA rats.

Figure 3:
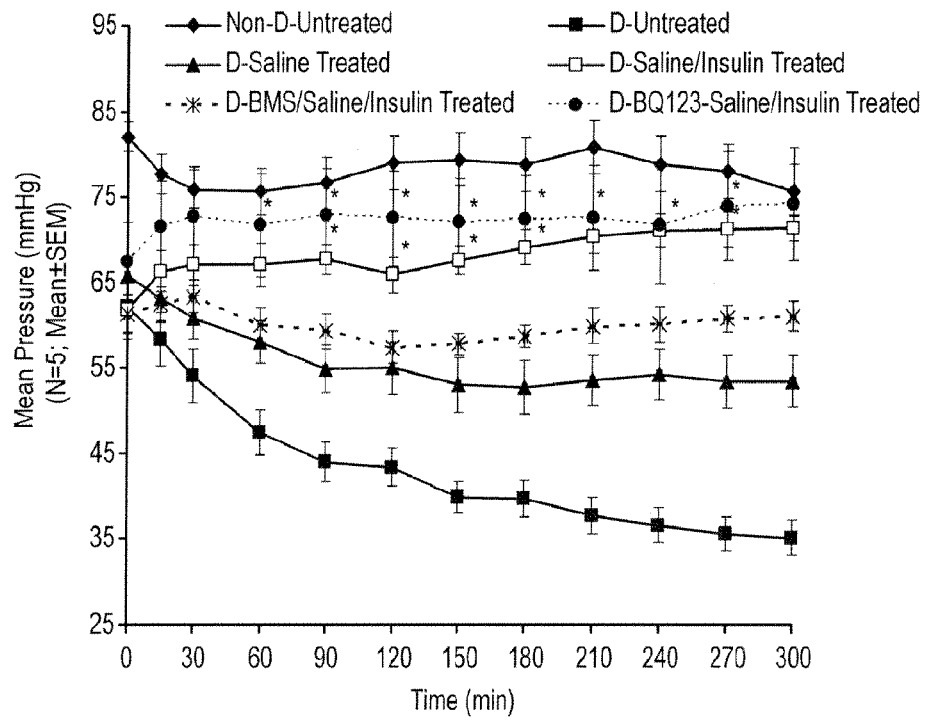
FIG. 3 contains graphs of mean arterial pressure (mmHg) vs. time for treated and untreated rats.

FIG. 3 shows the effect of induction of diabetic ketoacidosis and treatment on mean arterial pressure (mmHg) in various groups of rats. The arterial pressure in non-diabetic untreated rats was higher compared to diabetic ketoacidosis rats. Diabetic untreated rats showed a fall in arterial pressure till the end of experiment. Treatment with saline, saline+insulin, as well as BQ123+saline+insulin or BMS+saline+insulin, produced much less fall in arterial pressure compared to untreated rats. Treatment with saline+insulin, BQ123+saline+insulin or BMS+saline+insulin did not any fall in arterial pressure compared to baseline. It is concluded therefore that BQ123 and BMS-182874 stabilized the arterial pressure during treatment in diabetic ketoacidosis.

Figure 4:
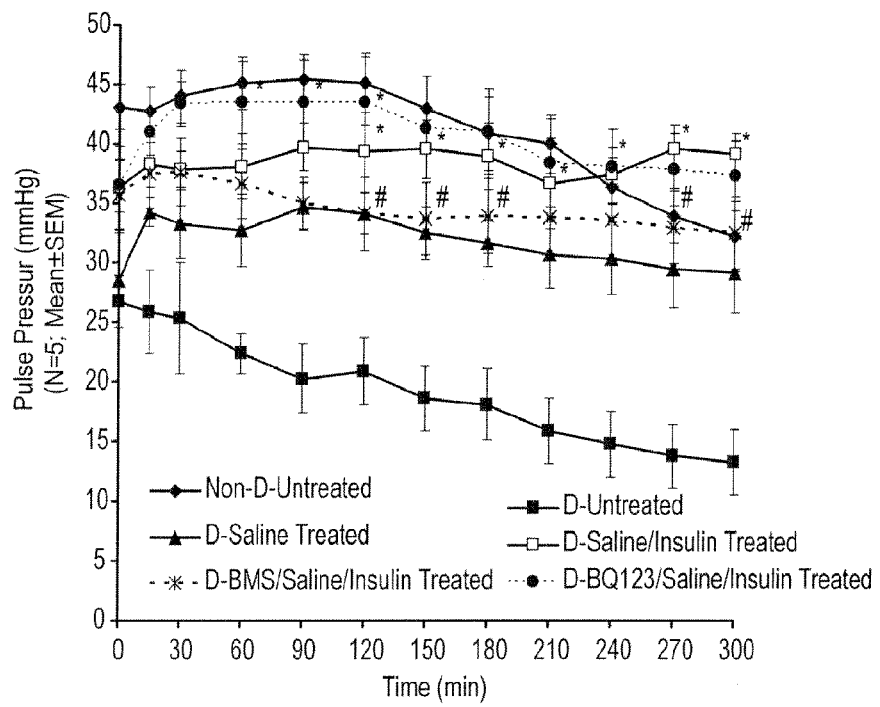
FIG. 4 contains graphs of mean pulse pressure (mmHg) vs. time for treated and untreated rats.

FIG. 4 shows the effect of induction of diabetic ketoacidosis and treatment on pulse pressure (mmHg) in various groups of rats. The pulse pressure in non-diabetic untreated rats was higher compared to diabetic ketoacidosis rats. Diabetic untreated rats showed a fall in pulse pressure until the end of experiment. Treatment with saline, saline+insulin, as well as BQ123+saline+insulin or BMS+saline+insulin, produced much less fall in pulse pressure compared to untreated rats. However, BQ123+saline+insulin treatment produced an increase in pulse pressure compared to baseline. It is concluded therefore that BQ123 and BMS-182874 stabilized the pulse pressure during treatment in diabetic ketoacidosis.

Figure 5:
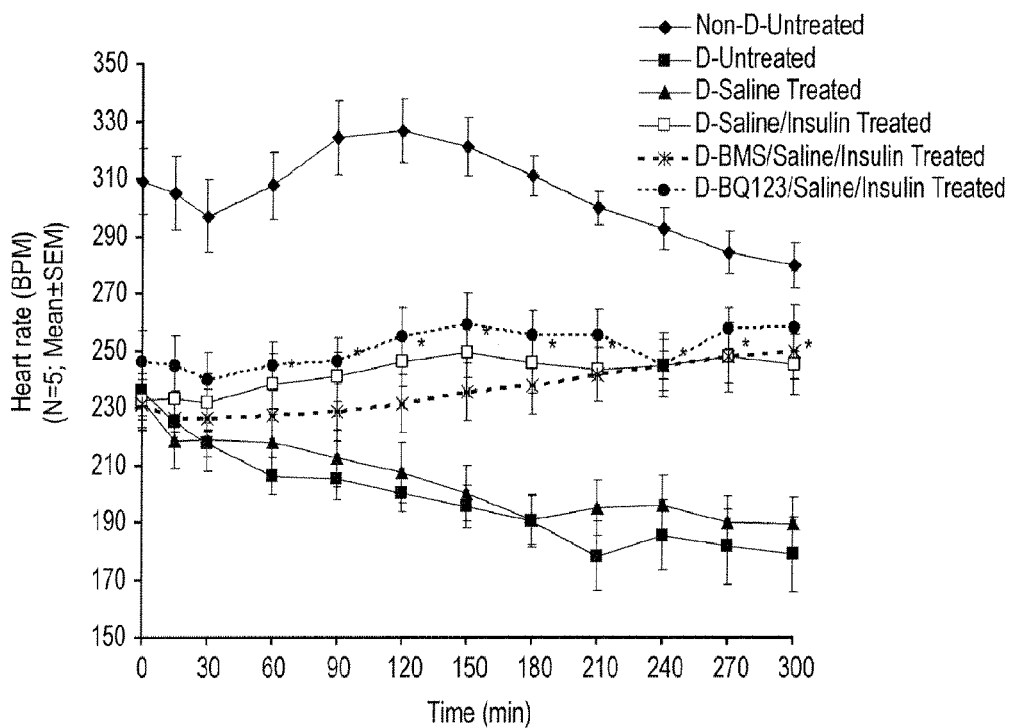
FIG. 5 contains graphs of heart rate (beats/minutes) vs. time for treated and untreated rats.

FIG. 5 shows the effect of induction of diabetic ketoacidosis and treatment on heart rate (beats/min) in various groups of rats. The heart rate in non-diabetic untreated rats was higher compared to diabetic ketoacidosis rats. Diabetic untreated rats showed a decrease in heart rate till the end of experiment. Treatment with saline produced a decrease in heart rate similar to that observed in untreated group. Treatment with saline+insulin or BMS+saline+insulin or BQ123+ saline+insulin did not produce any decrease in heart rate compared to baseline and was significantly (*P<0.05) higher than untreated or saline treated rats. Heart rate was similar in saline+insulin or BMS+saline+insulin or BQ123+saline+insulin treated groups.

Figure 6:
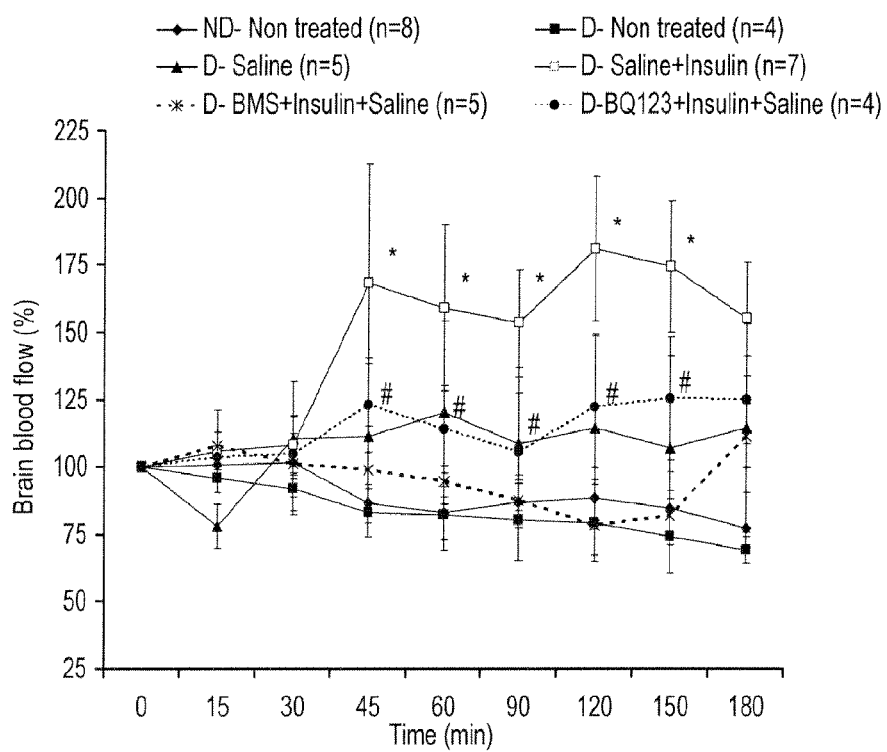
FIG. 6 contains graphs of % change in brain blood perfusion vs. time for treated and untreated rats.

FIG. 6 shows the effect of induction of diabetic ketoacidosis and treatment on cerebral blood perfusion (percent change) in various groups of rats. The cerebral blood perfusion was similar in non-diabetic untreated rats compared to diabetic ketoacidosis rats. Treatment with saline did not produce any significant effect on cerebral blood perfusion. However, saline+insulin treatment produced a marked (#P<0.05) increase in cerebral blood perfusion. This increase in cerebral blood perfusion could be significantly blocked by BMS-182874 or BQ123. BQ or BMS+saline+insulin treatment produced a significant (*P<0.05) attenuation of increase in cerebral blood perfusion compared to saline+insulin treated rats. It is concluded therefore that BQ or BMS-182874 stabilized the cerebral blood circulation during treatment in diabetic ketoacidosis. The life threatening risk during treatment of diabetic ketoacidosis is development of cerebral edema. An increase in cerebral blood perfusion can be a major contributing factor to the development of cerebral edema. The present results show for the first time that BQ or BMS-182874 can prevent an insulin-induced increase in cerebral blood perfusion in a rat model of diabetic ketoacidosis.

Figure 7:
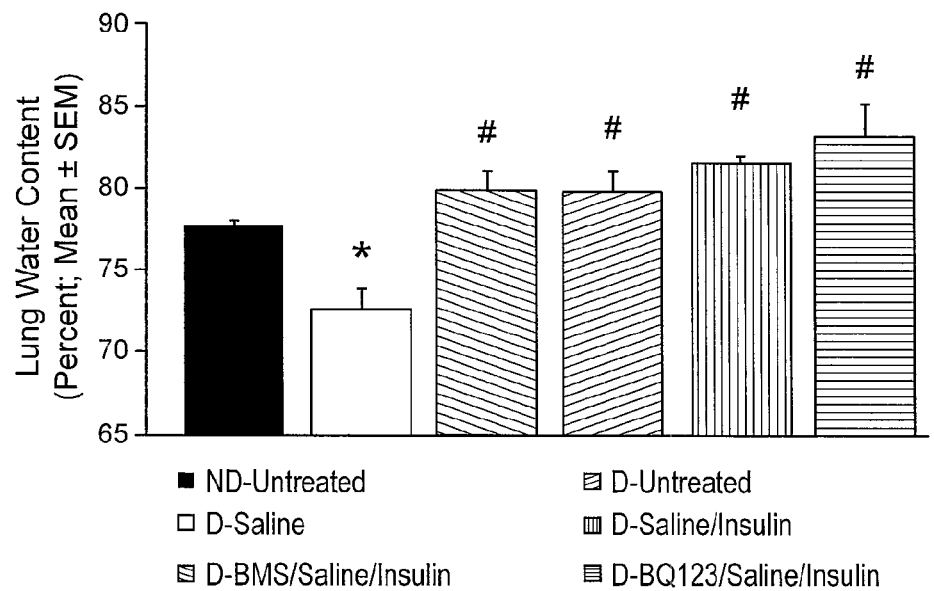
FIG. 7 contains bar graphs showing lung water content (%) for treated and untreated rats.

FIG. 7 shows the effect of induction of diabetic ketoacidosis and treatment on lung water content (pulmonary edema) in various groups of rats. The lung water content was significantly (*P<0.05) decreased in diabetic ketoacidosis rats compared to non-diabetic untreated rats. Treatment with saline, saline+insulin, or BQ or BMS+saline+insulin produced improvement in lung water content, and was significantly (#P<0.05) higher compared to diabetic ketoacidosis rats, but was similar to that observed in non-diabetic untreated rats. It is known that diabetic ketoacidosis produces severe dehydration, and hence a decrease in lung water content was observed. Infusion of saline, saline+insulin, or BQ or BMS+saline+insulin restored lung water content, and there was no evidence of pulmonary edema observed in any group.

Figure 8:
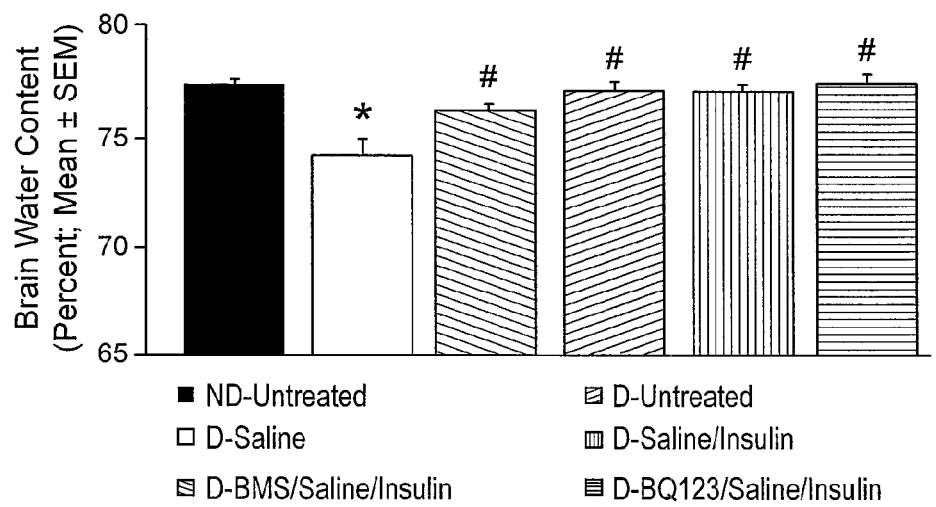
FIG. 8 contains bar graphs showing brain water content (%) for treated and untreated rats.

FIG. 8 shows the effect of induction of diabetic ketoacidosis and treatment on brain water content (cerebral edema) in various groups of rats. The brain water content was significantly (*P<0.05) decreased in diabetic ketoacidosis rats compared to non-diabetic untreated rats. Treatment with saline, saline+insulin, or BQ123 or BMS+saline+insulin produced improvement in brain water content and was significantly (#P<0.05) higher compared to diabetic ketoacidosis rats, but was similar to that observed in non-diabetic untreated rats. It is known that diabetic ketoacidosis produces severe dehydration, and hence a decrease in brain water content was observed. Infusion of saline, saline+insulin, or BQ or BMS+saline+insulin restored brain water content, and there was no evidence of cerebral edema observed in any group.

Figure 9:
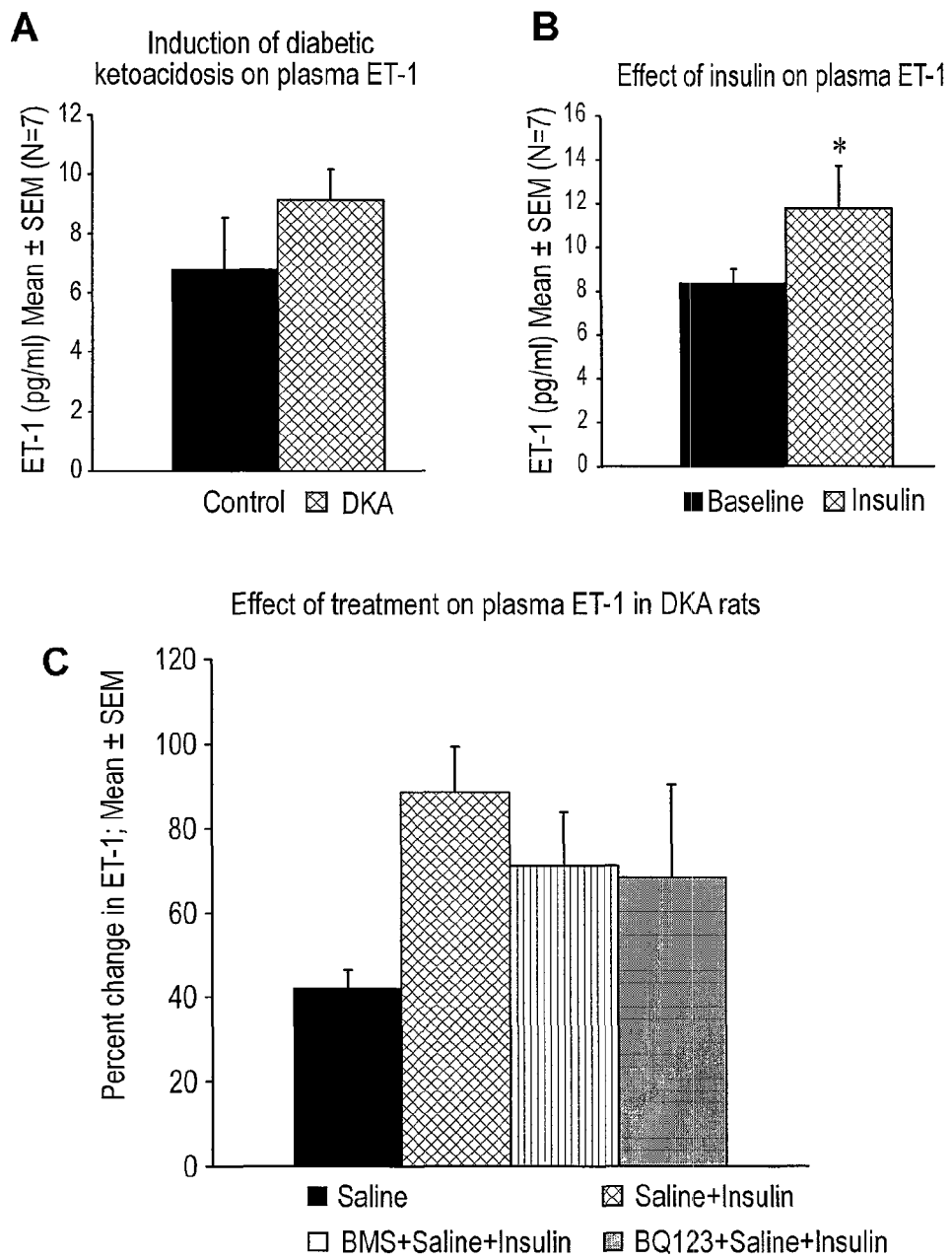
FIG. 9 contains bar graphs showing (a) ET-1 levels (pg/mL) due to induction of diabetic ketoacidosis (FIG. 9A), (b) ET-1 levels (pg/mL) as a result of insulin treatment (FIG. 9B), and (c) the percent change in ET-1 level results from three different treatments (FIG. 9C).

FIG. 9 shows the effect of induction of diabetic ketoacidosis and treatment on plasma ET-1 (pg/mL) levels in various groups of rats. *P<0.05 compared to baseline. It can be concluded that insulin treatment increased the plasma levels of ET-1, and all treatments produced similar increase in plasma ET-1 levels.

The above tests and data show the DKA was successfully induced in rats, as demonstrated by increased blood glucose, ketone and urine ketone levels, and decreased blood pH. Saline and insulin treatment produced significant reduction in blood glucose and ketones, and increased cerebral blood flow. An $ET_A$ receptor antagonist, e.g., BQ123 or BMS182874, prevented an insulin induced increase in cerebral blood perfusion in a rat model of DKA.

The life threatening risk during treatment of DKA is development of CE. An increase in cerebral blood perfusion can be a major contributing factor to the development of CE. It has been demonstrated for the first time show that an $ET_A$ receptor antagonist, e.g., BQ123 or BMS-182874, can prevent insulin induced increase in cerebral blood perfusion. The administration of a selective $ET_A$ receptor antagonist in the treatment of DKA will significantly reduce patient morbidity and mortality.

These findings further are supported by the fact that chronic treatment with a selective $ET_A$ receptor antagonist, in Goto Kakizaki rat (a model of Type II diabetes), markedly reduced hyperglycemia and restored plasma glucose clearance rates towards normal which could be from an improvement in insulin sensitivity (Balsiger et al., 2002). On the other hand, involvement of ET-1 in diabetic complications was determined in non-insulin-dependent diabetes mellitus patients, and no significant difference in plasma ET-1 levels among all diabetic patients, with or without angiopathy, with or without hypertension compared to healthy subjects (Bertello et al., 1994).

Diabetic ketoacidosis is the result of increased levels of ketones, acetoacetate, and β-hydroxybutyrate. Initially β-hydroxybutyrate exceeds acetoacetate by a ratio of 3:1, probably due to lack of β-hydroxybutyrate utilization (Nosadini et al., 1985), but the β-hydroxybutyrate decreases during treatment of diabetic ketoacidosis (Stephens et al., 1971). β-Hydroxybutyrate and acetoacetate cross the blood-brain barrier (BBB) through mono-carboxylic acid transport system (Poole and Halestrap, 1993). The concentration of ketones in blood influences the passage across the BBB and are used by specific brain regions (Hawkins and Biebuyck, 1979; Kreis and Ross, 1992). It has been demonstrated that ketones have an acute potentially deleterious effect on the cerebral blood vessels which could be due to acetoacetate-induced production of ET-1 (Isales et al., 1999).

It has been shown that ET-1 increased the permeability of human cerebrovascular endothelium (Stanimirovic et al., 1994). Several studies show that ET-1 regulates BBB. Application of ET-1 in the ischemic cortex following middle cerebral artery occlusion in rat could reduce the transfer co-efficient of small molecules across the BBB (Chi et al., 2001). P-glycoprotein is a critical element of the BBB, and ET-1 was found to rapidly reduce the transport mediated by P-glycoprotein at the BBB (Hartz et al., 2004). In another study it was found that, although ET-1 had no effect on P-glycoprotein expression, it does modulate the transport activity in human brain microvascular endothelial cells (Hembury and Mabondzo, 2008). Transgenic mice over expressing endothelial ET-1 displayed increased matrix metalloproteinase-2 expression, water content, and immunoglobulin leakage and decreased occluding level, indicating a breakdown of BBB (Leung et al., 2009). Repeated intracisternal administration of ET-1 in dogs and rats markedly increase the BBB permeability, which could be blocked by $ET_A$ receptor antagonist, S-0139 (Narushima et al., 2003). ET-1 has been associated with the development of cerebral edema in patient with acute ischemic stroke treated with t-PA and has been suggested to be a diagnostic marker for the development of severe brain edema (Moldes et al., 2008). Studies in rat model of embolic stroke where rtPA was used treatment with S-0139 provided neuroprotection by suppressing rtPA evoked disruption of BBB (Zhang et al., 2008).

In view of the above data, administration of a selective $ET_A$ receptor antagonist in the treatment of diabetic ketoacidosis should significantly reduce the morbidity and mortality of patients.

Modifications and variations of the invention as hereinbefore set forth can be made without departing from the spirit and scope thereof, and, therefore, only such limitations should be imposed as are indicated by the appended claims.

REFERENCES

B Balsiger et al. *Clin Sci (Lond)* 103 Suppl 48:430 S-433S (2002).
P Bertello et al. *Diabetes Care* 17:574-577 (1994).
S T Bonvallet et al. *Am J Physiol* 266:H1327-1331 (1994).
R Brondani et al. *Clin Biochem* 40:282-284 (2007).
O Z Chi et al. *Exp Brain Res* 141:1-5 (2001).
Y Ding et al. *Endocrine* 30:121-127 (2006).
C Ferri et al. *Diabetes Care* 19:504-506 (1996).
M Fulop *N Engl J Med* 300:1087-1089 (1979).
A Gulati et al. *Neuropeptides* 31:301-309 (1997a).
A Gulati et al. *Am J Physiol* 273:H1177-1186 (1997b).
T Haak et al. *Am J Hypertens* 5:161-166 (1992).
A M Hartz et al. *Mol Pharmacol* 66:387-394 (2004).
R A Hawkins et al. *Science* 205:325-327 (1979).
A Hembury et al. *Cell Mol Neurobiol* 28:915-921 (2008).
C Herbst et al. *Br J Pharmacol* 115:753-760 (1995).
C M Isales et al. *J Diabetes Complications* 13:91-97 (1999).
G Kirilov et al. *Horm Metab Res* 26:119-120 (1994).
E J Krane *Crit Care Med* 16:100 (1988).
R Kreis et al. *Radiology* 184:123-130 (1992).
T I Lam et al. *Diabetes* 54:510-516 (2005).
J W Leung et al. *Brain Res* 1266:121-129 (2009).
A C Lo et al. *J Cereb Blood Flow Metab* 25:998-1011 (2005).
A Malamitsi-Puchner et al. *J Pediatr Endocrinol Metab* 9:463-468 (1996).
J I Malone et al. *Diabetes Care* 3:543-547 (1980).
O Moldes et al. *Stroke* 39:2006-2010 (2008).
T Morise et al. *Diabetes Care* 18:87-89 (1995).
I Narushima et al. *Pharmacol Toxicol* 92:21-26 (2003).
R Nosadini et al. *Am J Physiol* 248:R611-620 (1985).
P T Nowicki et al. *J Pediatr* 146:805-810 (2005).
R C Poole et al. *Am J Physiol* 264:C761-782 (1993).
P Poulat et al. *Eur J Pharmacol* 344:251-259 (1998).
S A Said et al. *Pharmacol Res* 51:107-115 (2005).
J M Sasser et al. *J Am Soc Nephrol* 18:143-154 (2007).
J G Schneider et al. *Am J Hypertens* 15:967-972 (2002).
N A Sherry et al. *Paediatr Drugs* 10:209-215 (2008).
S M Silver et al. *Kidney Int* 51:1237-1244 (1997).
D B Stanimirovic et al. *Acta Neurochir Suppl (Wien)* 60:71-75 (1994).
J M Stephens et al. *Diabetes* 20:485-489 (1971).
K Takahashi et al. *Diabetologia* 33:306-310 (1990).
M Vanelli M and Chiarelli F (2003) *Acta Biomed* 74:59-68.
L A Vazquez et al. *J Diabetes Complications* 13:325-331 (1999).
J Wolfsdorf et al. *Pediatr Diabetes* 8:28-43 (2007).
M Yanagisawa et al. *J Hypertens Suppl* 6:S188-191 (1988a).
M Yanagisawa et al. *Nature* 332:411-415 (1988b).
N Yuen et al. *Diabetes* 57:2588-2594 (2008).
R L Zhang et al. *Stroke* 39:2830-2836 (2008).

APPENDIX A

Selective $ET_A$ Antagonists

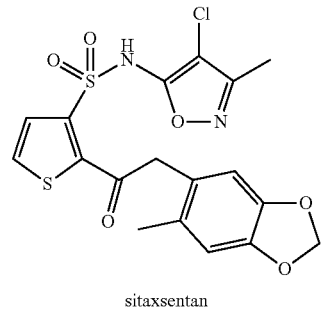

1 sitaxsentan

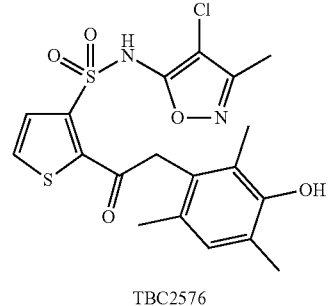

2

TBC2576

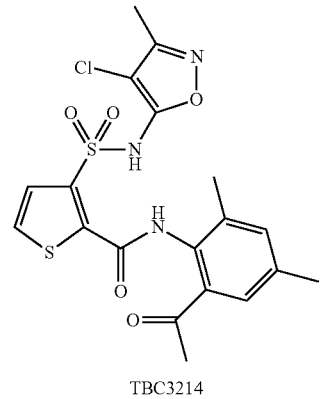

3

TBC3214

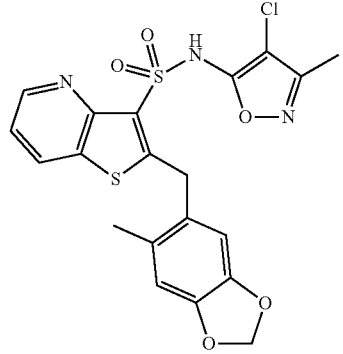

4

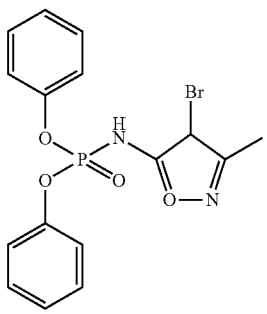
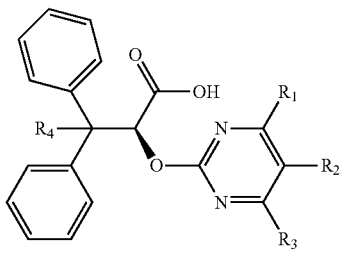
6 $R_1 = R_3 = R_4 = CH_3$, $R_2 = H$
7 $R_1 = R_3 = R_4 = OCH_3$, $R_2 = F$
8 $R_1 = OCH_3$, $R_2 = H$, $R_3 = CH_3$, $R_4 = -OCH_2CON(CH_3)C_6H_5$
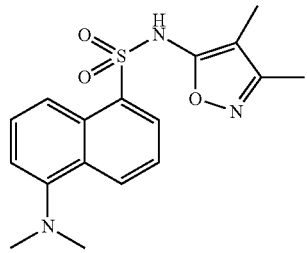
BMS 182,874
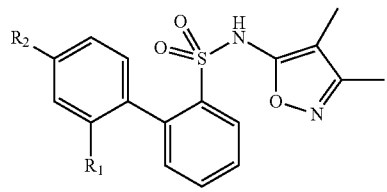
10 $R_1 = CH_2OH$, $R_2 = H$
11 $R_1 = H$, $R_2 = $ 2-oxazolyl
12 $R_1 = H$, $R_2 = $ 2-pyrimidinyl
13 $R_1 = H$, $R_2 = $ 4-methoxyethoxymethyl-4-oxo-1,2,4-triazol-2-yl
14 $R_1 = H$, $R_2 = $ 1,3-diazo-2-butyl-4-oxospiro (4,4)-1-nonen-3-ylmethyl
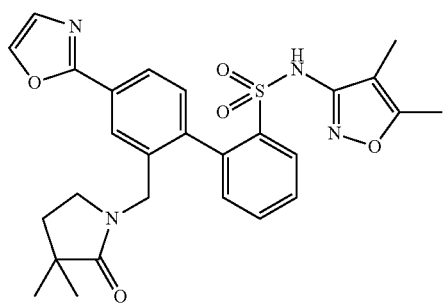
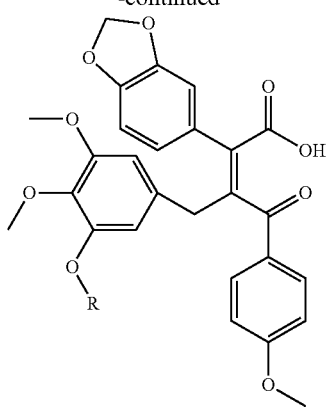
16 $R = CH_3$ (PD156707)
17 $R = CH_2CH_2CH_2SO_3H$
18 $R = OCH_2CH_2CH_2SO_3H$
19 $R = OCONHCH_2CO_2C_2H_5$
PD180988

-continued
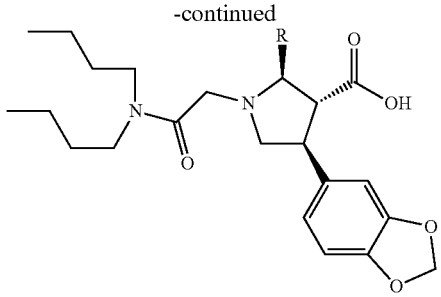
22 R = C₆H₄-4-OCH₃ (ABT-627)
23 R = CH₂CH₂-2-pyridyl
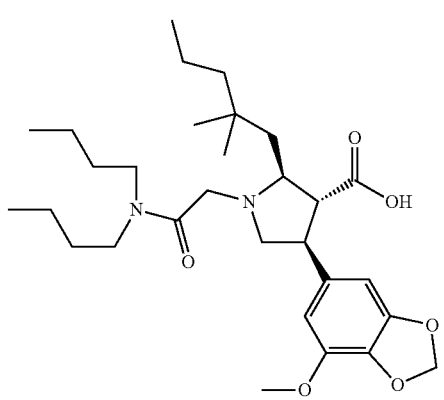
ABT-546
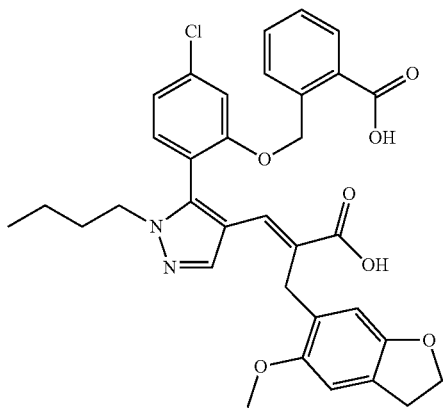
SB247083
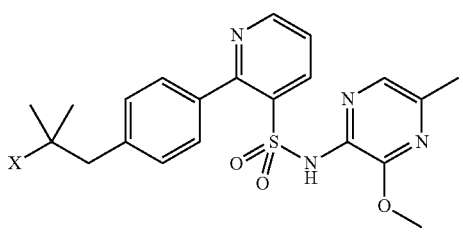
26 X = CO₂H (Z1611)
27 X = H
-continued
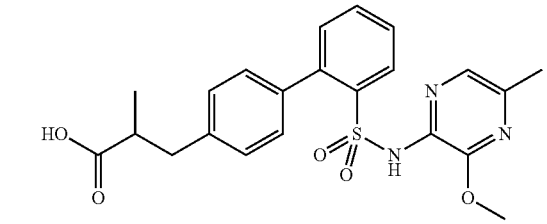
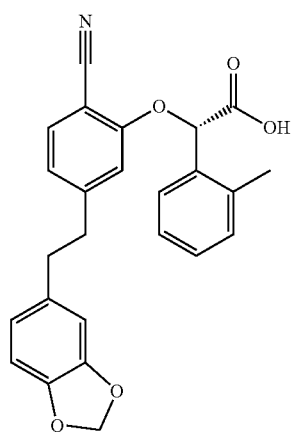
RPR118031A
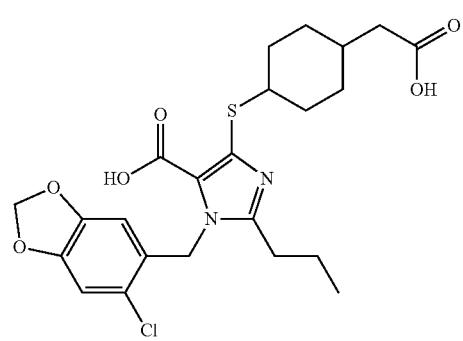
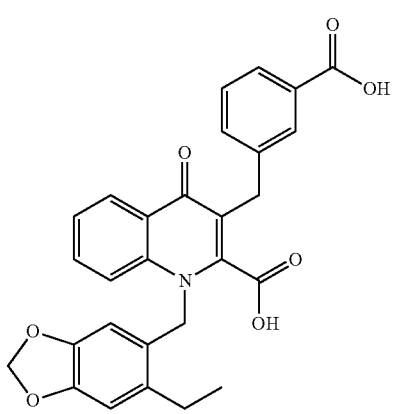

-continued
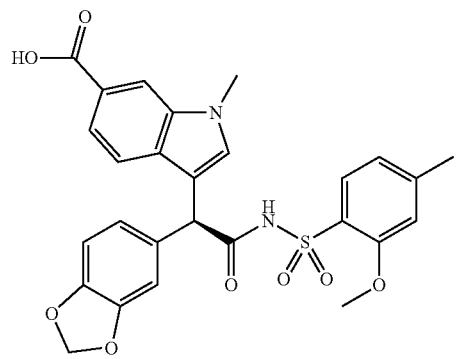
32
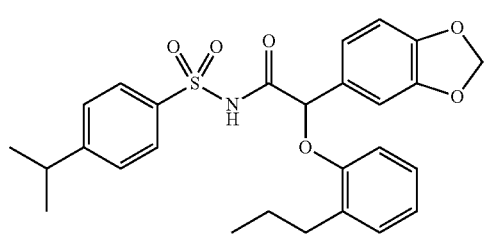
33
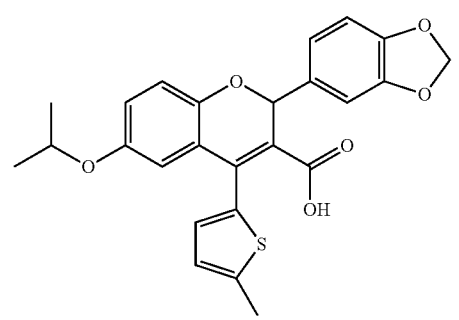
34
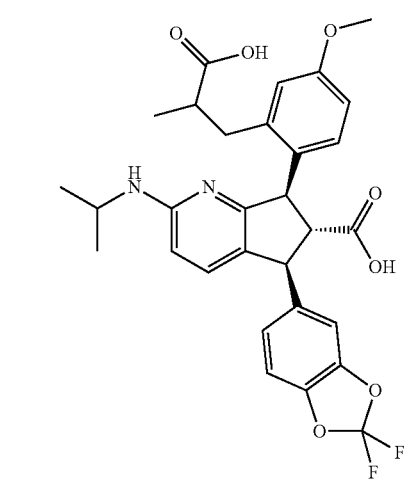
35
APPENDIX B
Balanced $ET_A/ET_B$ Antagonists
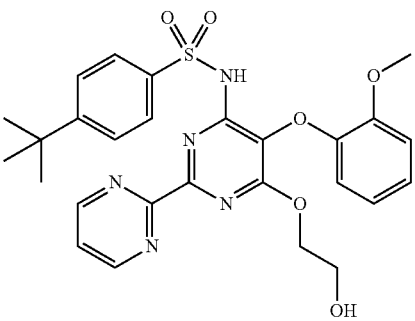
46
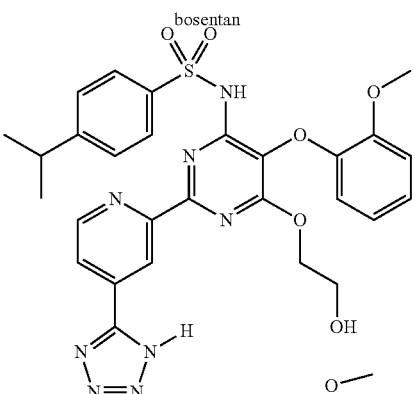
47 bosentan
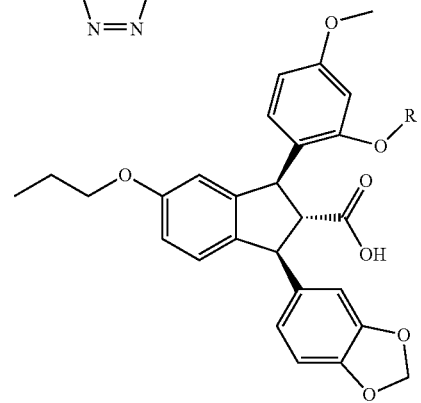
48 R = CH$_2$CO$_2$H SB209670
49 R = CH$_2$CH$_2$OH SB217242
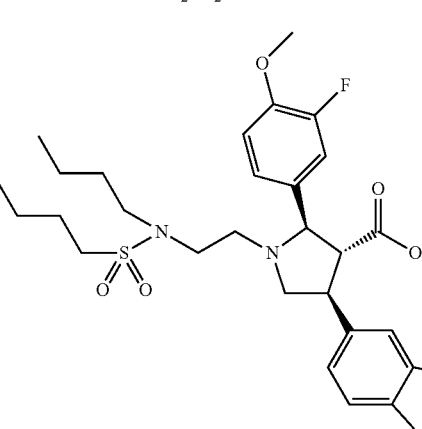
50

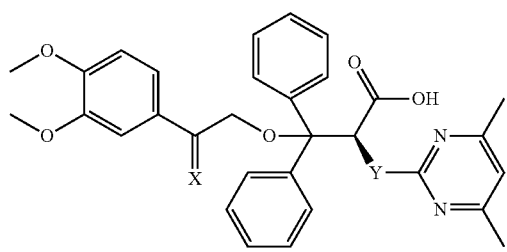
51 X = H₂, Y = CH₂ S-LU 302872
52 X = O, Y = O
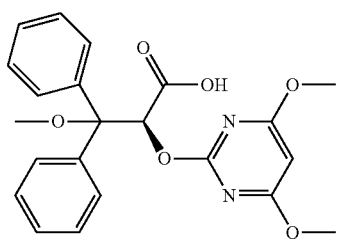
53
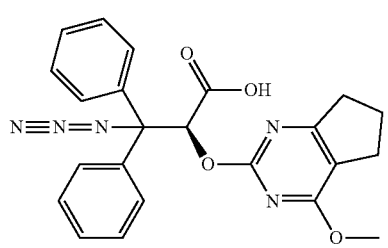
54
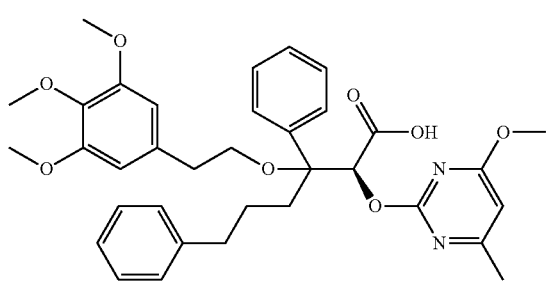
55
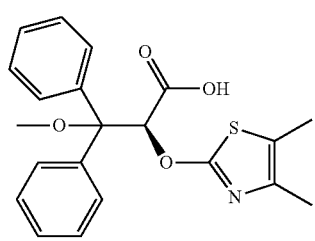
56
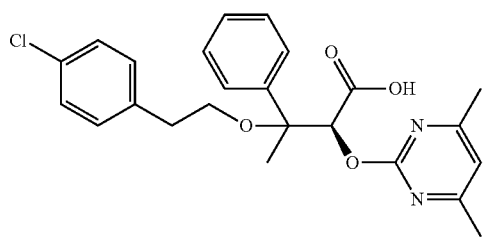
57
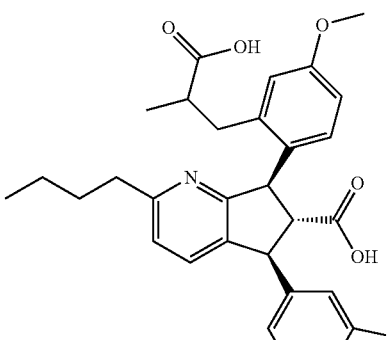
58
J-104132
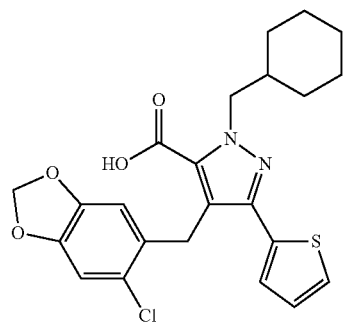
59
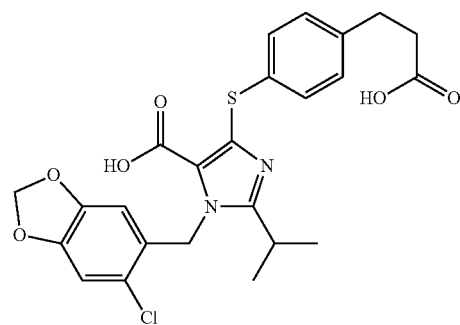
60
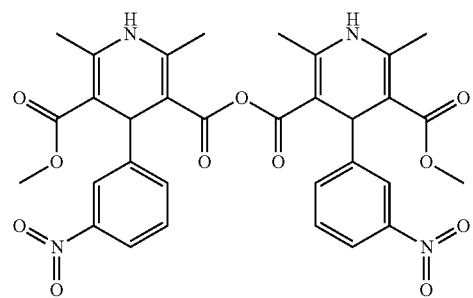
61

-continued
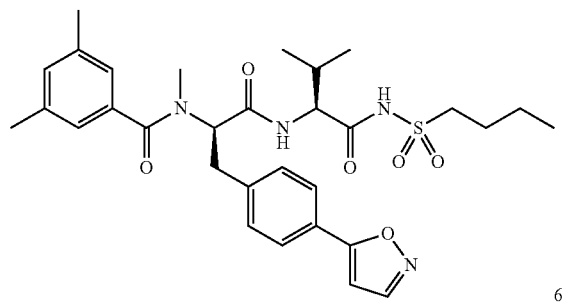
62
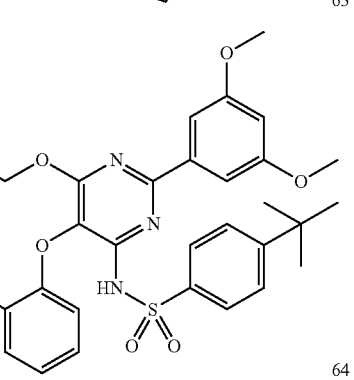
63
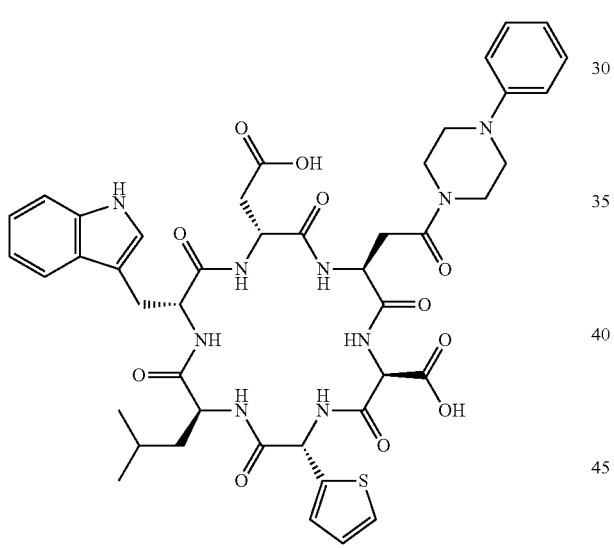
TAK-044
64
-continued
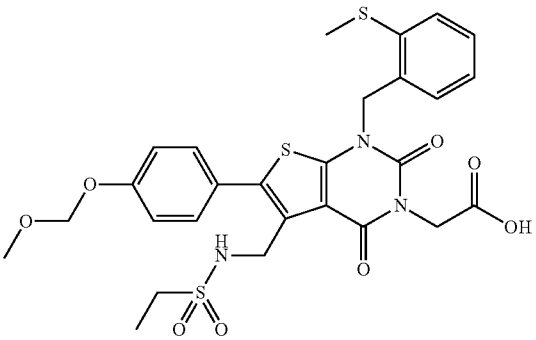
66
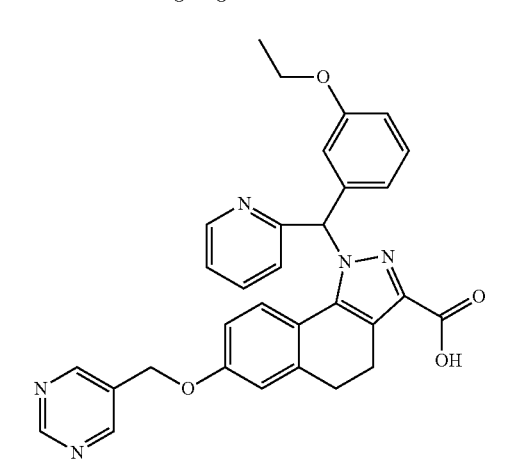
67
APPENDIX C
Selective ET$_B$ Antagonists
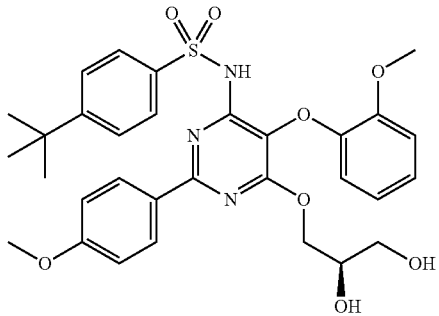
36
Ro 46-8443
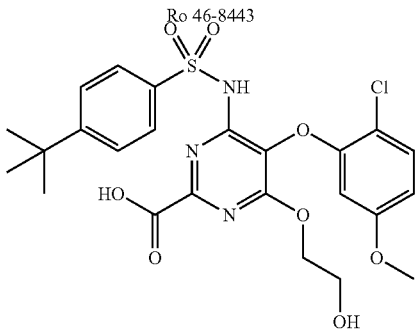
37

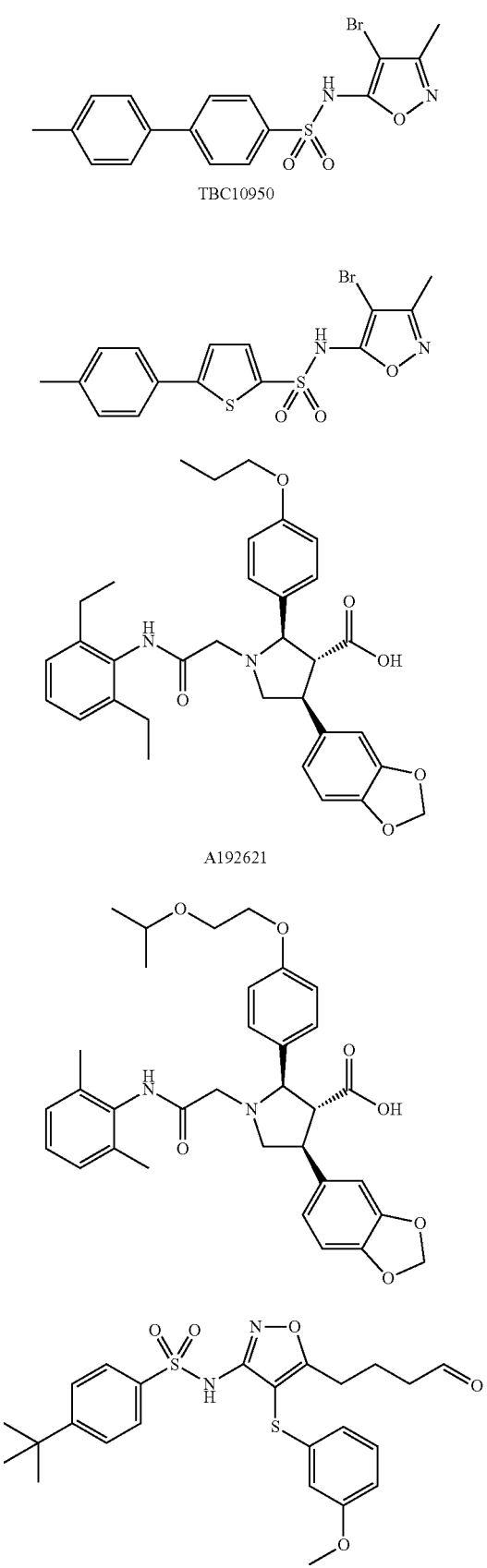
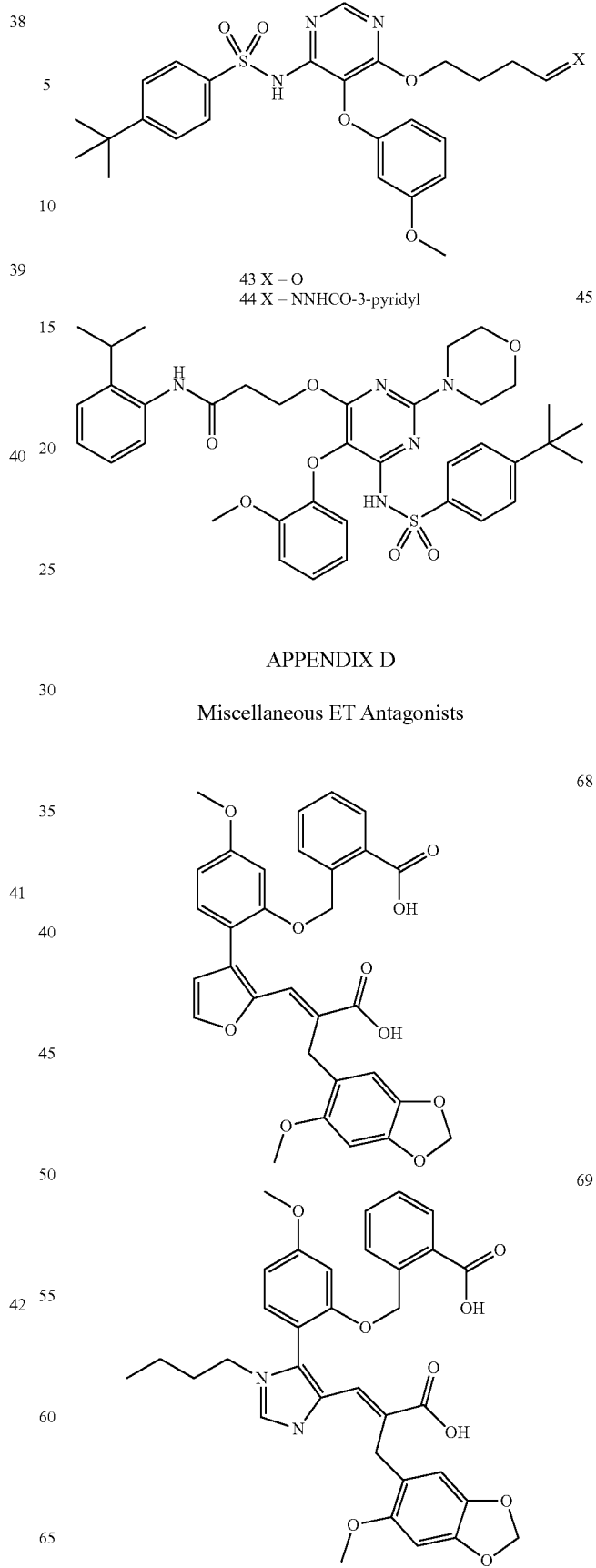

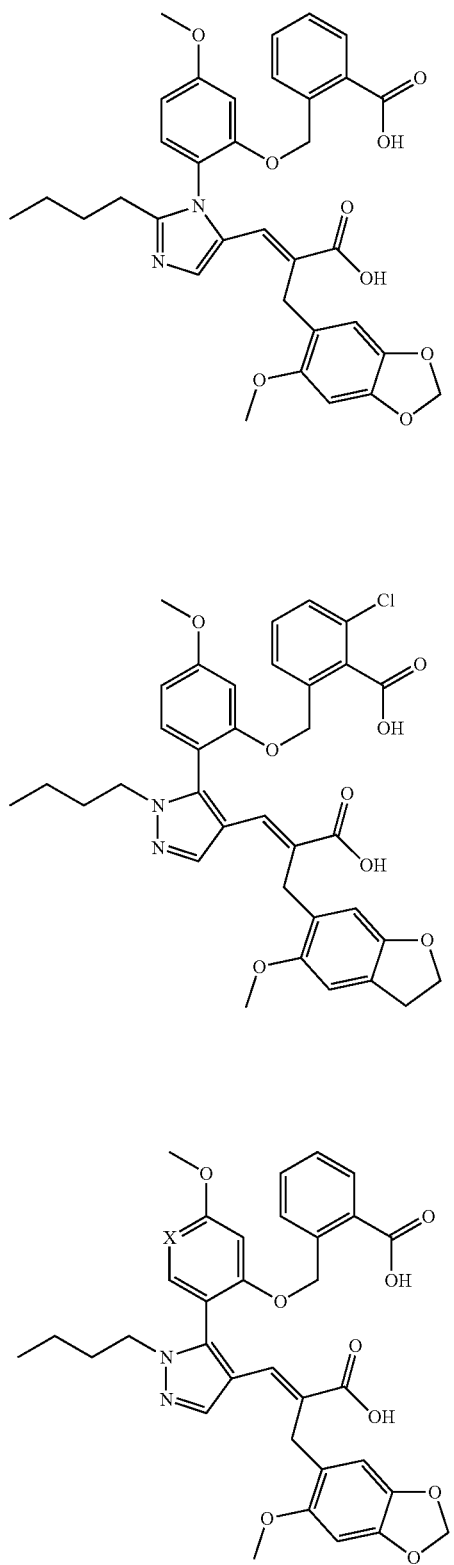
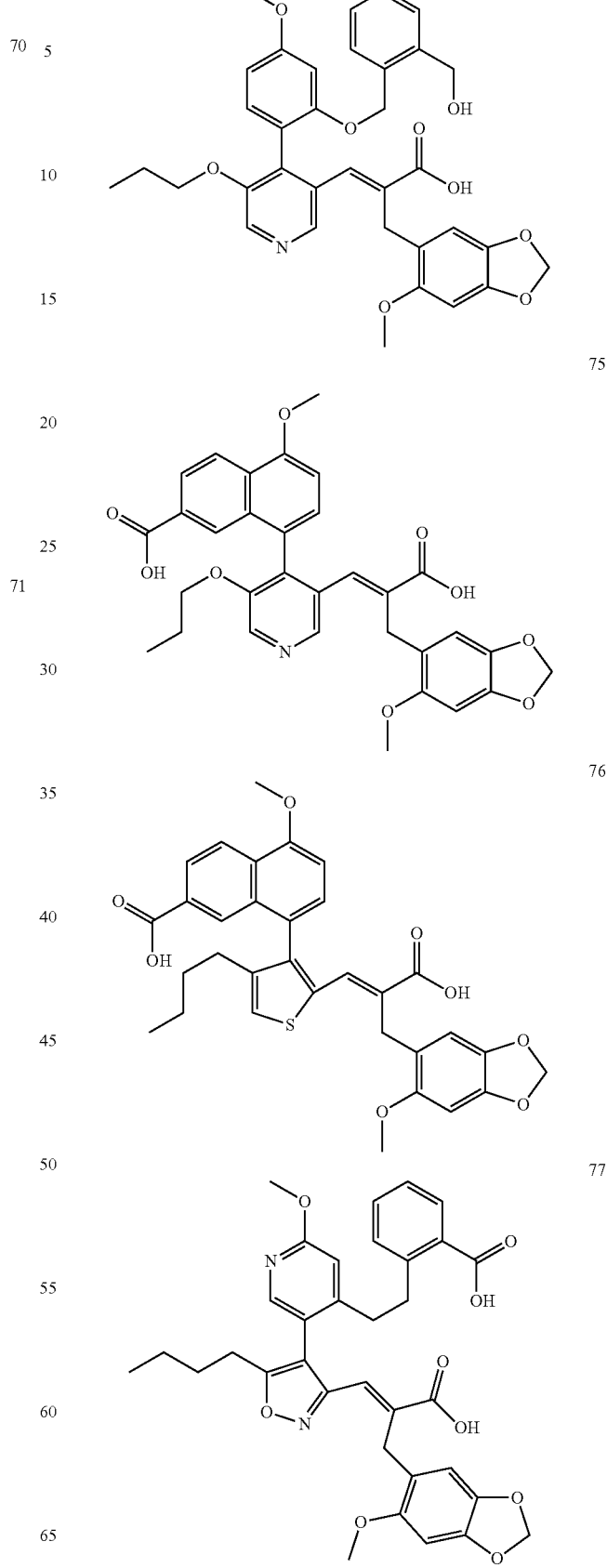

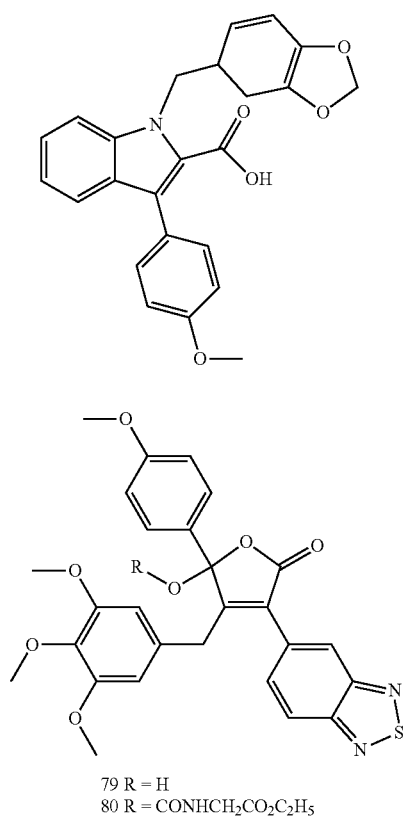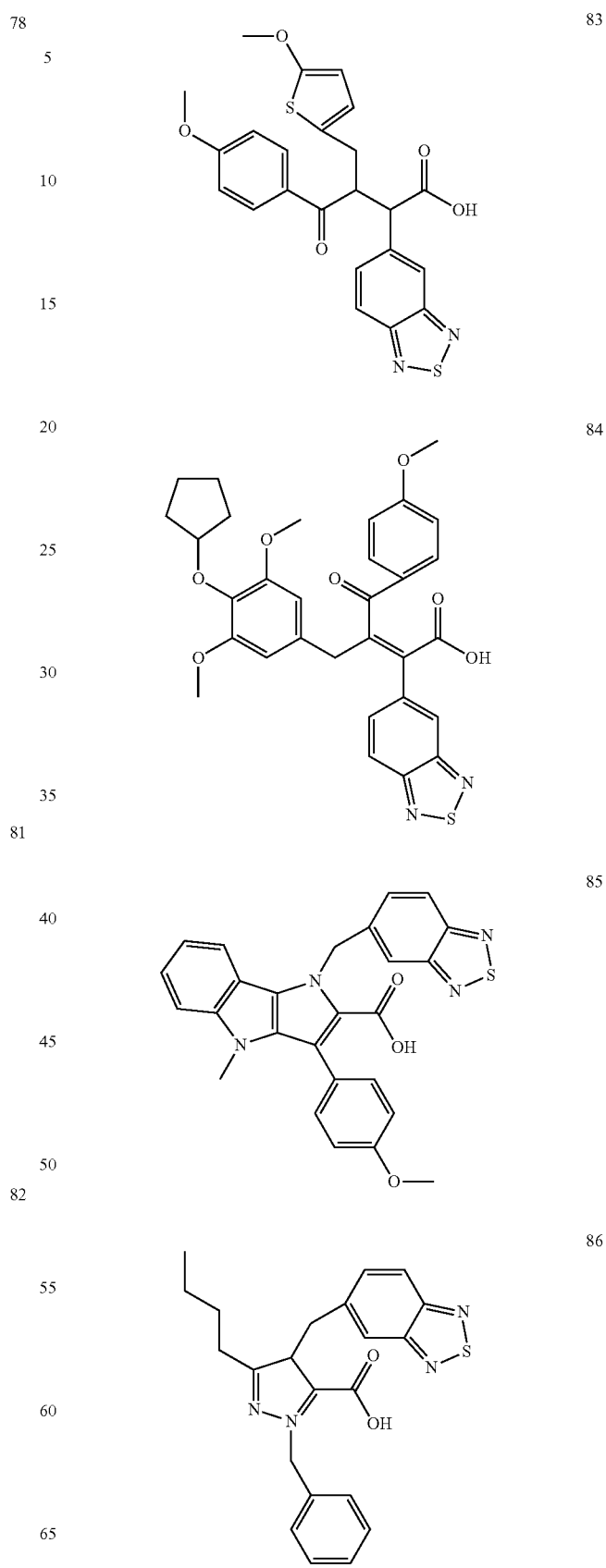

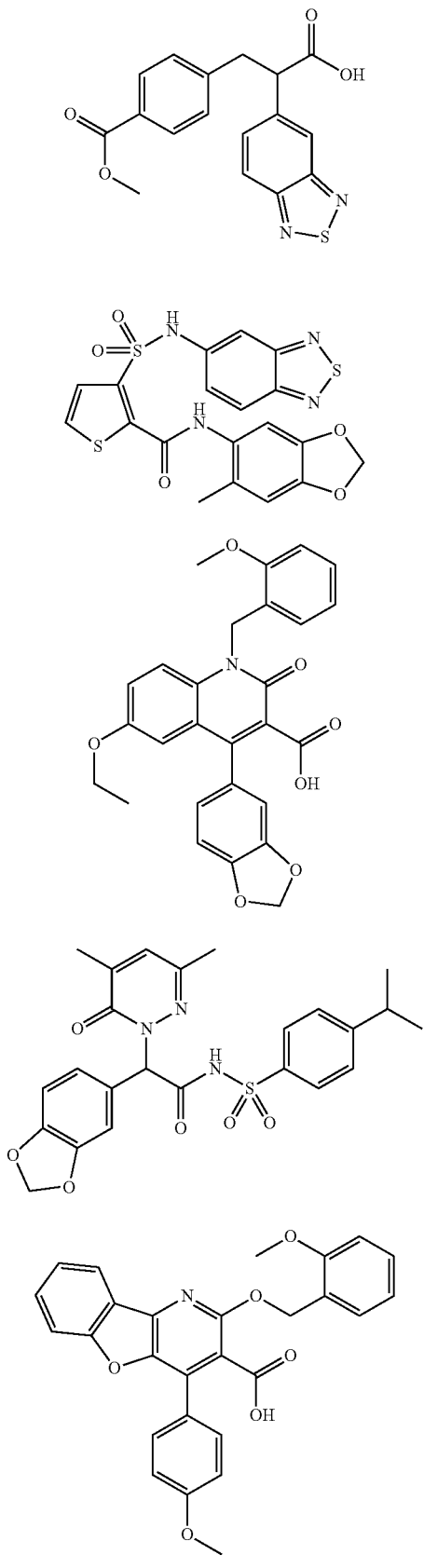
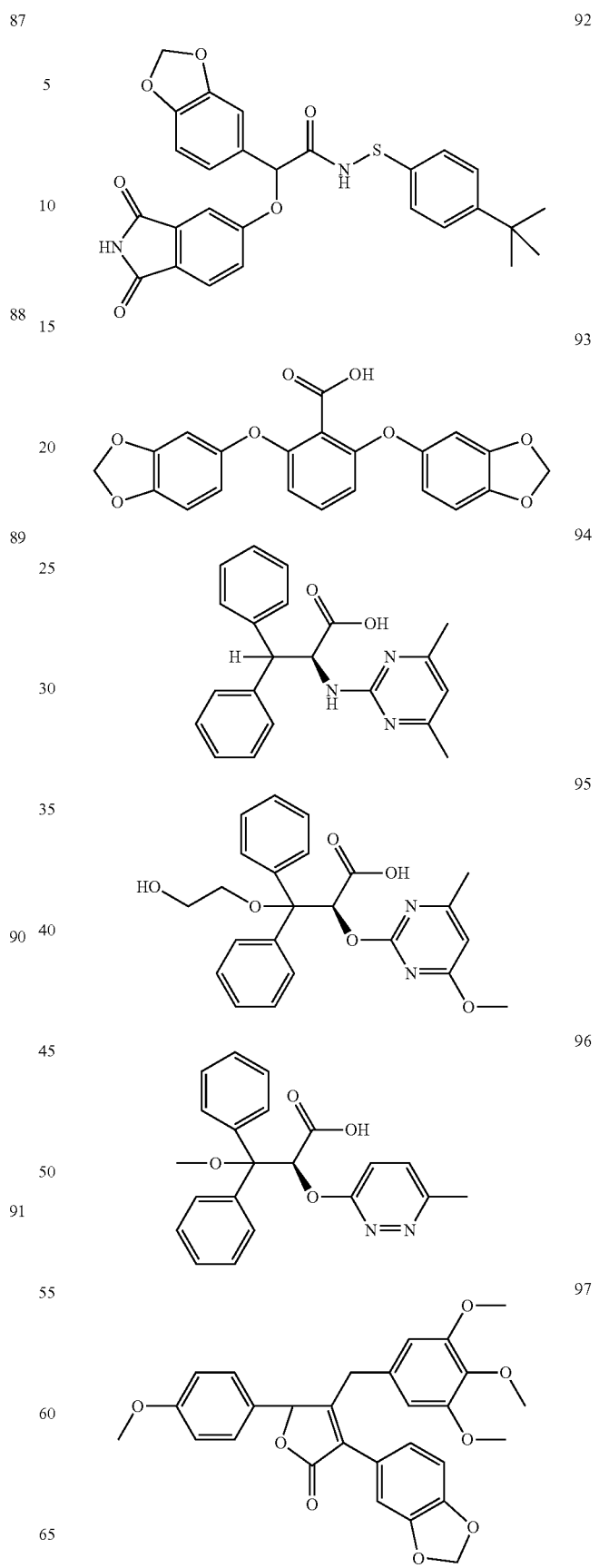

98
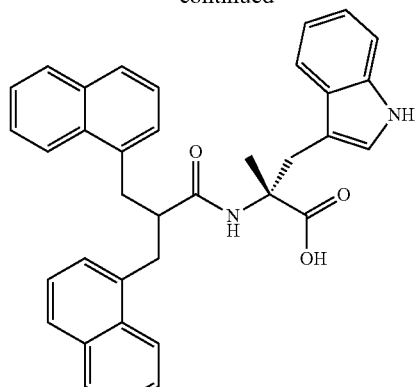
99
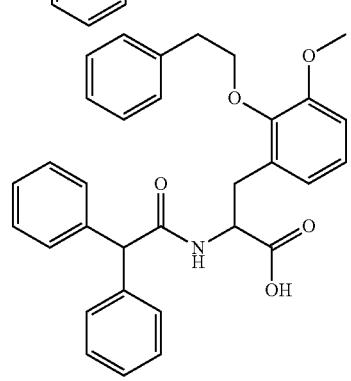
100
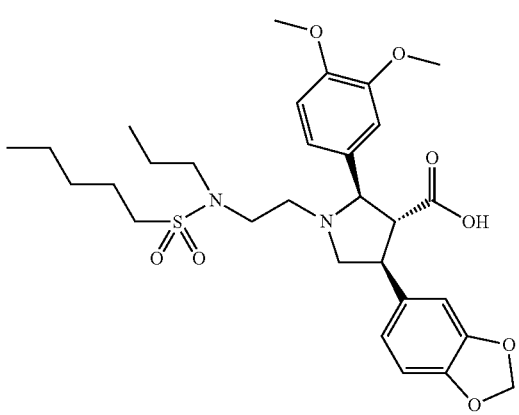
101
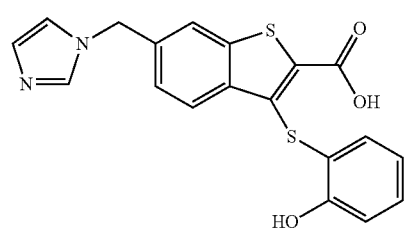
102
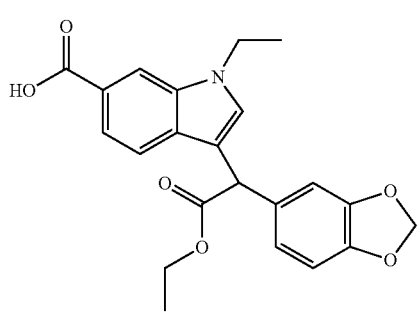
103
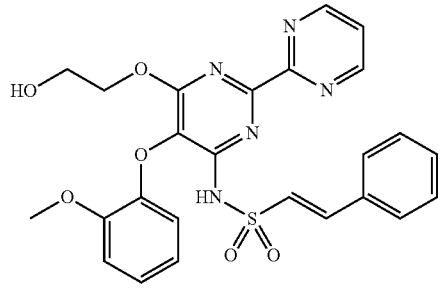
104
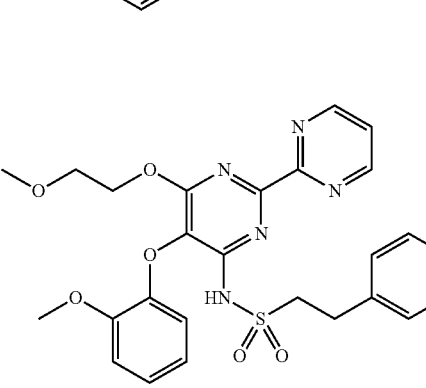
105
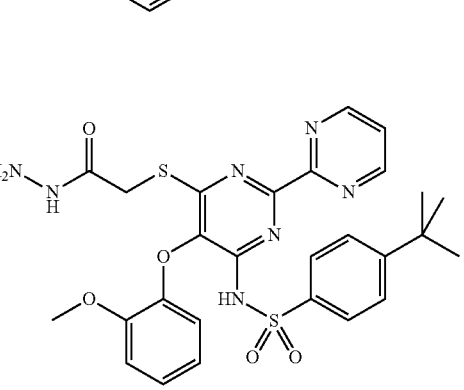
106
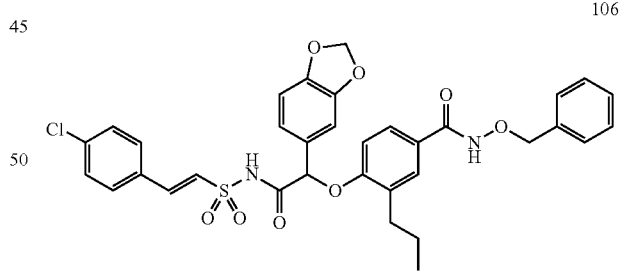
107
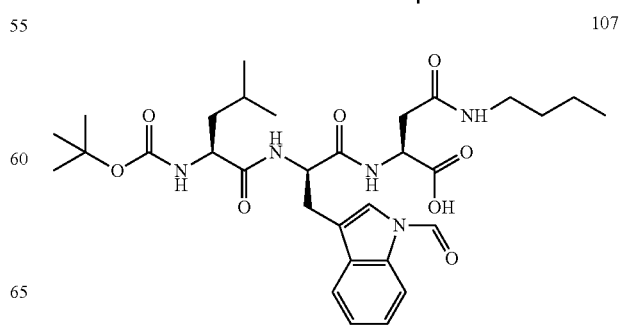

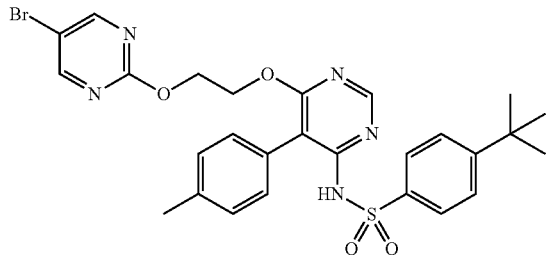
108

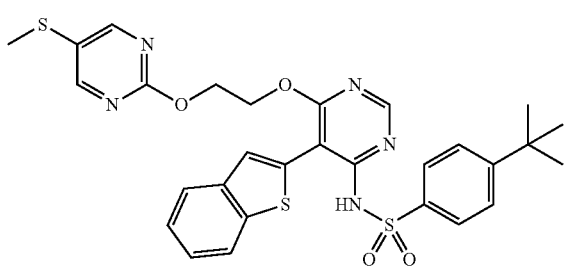
109

What is claimed is:

1. A method of treating diabetic ketoacidosis comprising administering to a mammal in need thereof a therapeutically effective amount of BQ123.

2. The method of claim 1 wherein the mammal is undergoing an insulin therapy to treat diabetes.

3. The method of claim 1 wherein the mammal is a human.

4. The method of claim 1 wherein the endothelin antagonist is administered as a sole therapy for diabetic ketoacidosis.

5. The method of claim 1 wherein the endothelin antagonist is administered in conjunction with a therapy for treating diabetes and/or a second therapy for treating diabetic ketoacidosis.

6. The method of claim 5 wherein the therapy for treating diabetes and the second therapy for treating diabetic ketoacidosis are selected from the group consisting of insulin, electrolytes, sodium bicarbonate, a diuretic, bumetanide, mannitol, hypertonic saline, and mixtures thereof.

7. The method of claim 5 wherein the endothelin antagonist is administered before, after, or simultaneously with the diabetes therapy and/or the second therapy for diabetic ketoacidosis.

* * * * *